US006673556B2

(12) United States Patent
Nixon et al.

(10) Patent No.: US 6,673,556 B2
(45) Date of Patent: Jan. 6, 2004

(54) METHODS OF DETECTING SPECIFIC CELL LYSIS

(75) Inventors: Douglas Nixon, San Francisco, CA (US); Adrian B. McDermott, Leyburn (GB); Scott Furlan, San Francisco, CA (US); Martin Bigos, San Francisco, CA (US); Megan Sheehy, Syracuse, NY (US); Paul Klenerman, Oxford (GB)

(73) Assignee: The J. David Gladstone Institutes, San Francisco, CA (US)

( * ) Notice: Subject to any disclaimer, the term of this patent is extended or adjusted under 35 U.S.C. 154(b) by 56 days.

(21) Appl. No.: 09/954,392

(22) Filed: Sep. 12, 2001

(65) Prior Publication Data

US 2002/0146746 A1 Oct. 10, 2002

Related U.S. Application Data

(60) Provisional application No. 60/282,258, filed on Apr. 5, 2001.

(51) Int. Cl.⁷ .......................... G01N 33/53; G01N 1/30; G01N 33/567; C12Q 3/00

(52) U.S. Cl. .......................... 435/7.2; 435/40.5; 435/4; 435/7.21

(58) Field of Search .......................... 435/4, 7.2, 40.5, 435/7.21

(56) References Cited

U.S. PATENT DOCUMENTS 4,444,879 A    4/1984   Foster et al.
6,348,580 B1 * 2/2002   Fukui et al.
6,459,805 B1 * 10/2002  Reynolds et al.

OTHER PUBLICATIONS

Ahmad, N. et al. Fusogenic potential of prokaryotic membrane lipids, European Journal of Biochemistry. Nov. 2001, vol. 268, No. 22, pp. 5667–5675.
Hoekstra et al. Flrourescence Method for Measuring the Kinetics of Fusion between Biological Membranes, Biochemistry. 1984, vol. 23, pp. 5675–5681.
Owais et al. Lipsome–mediated cytosolic delivery of macromolecules and its possible use in vaccine development. European Journal of Biochemistry. 2000, vol. 267, pp. 3946–3956.
Zhou et al. Induction of cytotoxic T lymphocytes in vivo with protein antigen entrapped in membranous vehicles. The Journal of Immunology. Sep. 1, 1992, vol. 149, No. 5, pp. 1599–1604.
Molecular Probes (Product Information), Live/Dead Cell Mediated Cytotoxicity Kit (L–7010), jan. 23, 2001.
Johann et al. (1995) *J. Immunol Methods* 185 :209–216.
Karawajew et al. (1994) *J. Immunol. Methods* 177 :119–130.
King and Raddicchi–Mastroianni (1996) *Cytometry* 24 : 368–373.
Larsson and Nygren (1989) *Anticancer Res.* 9: 1111–1119.
Lebow and Bonavida (1990) *Proc. Natl. Acad. Sci. USA* 87:6063–6067.
Lebow et al. (1986) *Nat. Immun. Cell Growth Regul.* 5 : 221–237.
Mattis et al. (1997) *J. Immunol. Methods* 204 :135–142.
Nociari et al. (1998) *J. Immunol. Methods* 213 :157–167.
Papa and Valentini (1994) *Methods Cell Bio.* 42 : 193–207.
Papadopoulos et al. (1994) *J. Immunol. Methods* 177 : 101–111.
Parish (1999) *Immunol Cell Biol.* 77 : 499–508.
Radcliff et al. (1991) *J. Immunol. Methods* 139 :281–292.
Radosevic et al. (1990) *J. Immul. Methods* 135 :81–89.
Radosevic et al. (1993) *J. Immunol. Methods* 135 :81–89.
Renno et al. (1999) *J. Immunol.* 162 :6312–6315.
Schafer et al. (1997) *J. Immul. Methods* 204 :89–84.
Shau and Dawson (1985) *J. Immunol.* 135 :137–140.
Slezak and Horan (1989) *J. Immunol. Methods* 117 : 205–214.
Song et al. (1999) *Transplantation* 68 :297–299.
Vangraft et al. (1993) *Cytometry* 14 :257–264.
Vitale et al. (1992) *J. Immunol. Methods* 149 :189–196.
Zamai et al. (1998) *Cytometry* 32 :280–285.
Aubry et al. (1999) *Cytometry* 37 :197–204.
Beavis and Pennline (1994) *J. Immunol. Methods* 170 : 57–65.
Callewaert et al. (1991) *Cytometry* 12 :666–676.
Cavarec et al. (1990) *J. Immunol. Methods* 130 :251–261.
Chang et al. (1993) *J. Immunol. Methods* 166 :45–54.
Chang et al. (1998) *J. Immunol. Methods* 211 :51–63.
Flieger et al. (1995) *J. of Immunol Methods* 180 : 1–13.
Flieger et al. (1999) *Hybridoma* 18 :63–68.
Ford et al. (1996) *J. Surg. Res.* 62 :23–28.
Garton and Schoenwolf (1996) *Anatomical Record* 244 : 112–117.
Goldberg et al. (1999) *J. Immul Methods* 224 :1–9.
Hasbold et al. (1998) Immunol. Cell Biol. 77 :516–522.
Hatam et al. (1994) *Cytometry* 16 : 59–68.

* cited by examiner

Primary Examiner—Christopher R. Tate
Assistant Examiner—Randall Winston
(74) Attorney, Agent, or Firm—Paula A. Borden; Bozicevic, Field & Francis, LLP

(57) ABSTRACT

The present invention provides methods of detecting specific lysis of a cell by a lytic agent. The methods generally involve contacting a labeled target cell with a lytic agent; and detecting fluorescence in the target cell. The target cells are labeled with two fluorescent labels: a first fluorescent label that labels the plasma membrane; and a second fluorescent label that labels the cytosol. Release of the cytosolic label from the target cell indicates that the target cell has been lysed. The invention further provides methods of detecting the presence in a sample of a cell that specifically lyses a target cell. The invention further provides methods of detecting the presence in a sample of an antibody that specifically lyses a target cell. The methods are useful in a variety of applications.

10 Claims, 9 Drawing Sheets

(a) M1 = 65.4% — Targets and effectors incubated for 4 hours without peptide.

(b) M1 = 32.3% — Peptide pulsed targets and effectors incubated for 4 hours

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Ser Leu Tyr Asn Thr Val Ala Thr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Gly Ile Leu Gly Phe Val Phe Thr Leu
1               5

METHODS OF DETECTING SPECIFIC CELL LYSIS

CROSS-REFERENCE

This application claims benefit of priority of U.S. Provisional Patent Application Ser. No. 60/282,258, filed Apr. 5, 2001, which application is incorporated herein by reference in its entirety.

STATEMENT REGARDING FEDERALLY SPONSORED RESEARCH

The U.S. government may have certain rights in this invention, pursuant to grant no. RO1-A146254 awarded by the National Institutes of Health.

FIELD OF THE INVENTION

The present invention is in the field of cellular biology, and in particular relates to cell lysis.

BACKGROUND OF THE INVENTION

Specific lysis of target cells is a feature of a number of normal physiological processes. For example, $CD8^+$ cytotoxic T lymphocytes (CTL) are central to the adaptive immune response against viruses, protozoa, intracellular bacteria, and in the rejection of allogeneic grafts. CTL recognize and kill target cells expressing antigen-derived peptides presented by class I major histocompatibility complex (MHC). In vivo, antigen specific $CD8^+$ T cells also exert effector activity through release of soluble cytokines and chemokines, which either signal other effector cells or have direct antiviral activity. Other cells have lytic activity and participate in the elimination of infected cells or, in some circumstances, self derived cells as in autoimmune diseases. These lytic cells include $CD4^+$ T lymphocytes with lytic effects, Natural Killer (NK) cells, Natural Killer T (NKT) cells and lymphokine activated killer (LAK) cells.

A number of cells that have cytotoxic potential express membrane receptors for the Fc region of an antibody molecule. When antibody is specifically bound to a target cell, receptor-bearing lytic cells bind to the target cell-bound antibody Fc region, and subsequently cause lysis of the target cell. Although the lytic cells are not themselves specific, the specificity of antibody directs them to the specific target cells, in a reaction known as antibody-dependent cell-mediated cytotoxicity (ADCC). Among the cells that can mediate ADCC are natural killer (NK) cell, macrophages, monocytes, neutrophils, and eosinophils. Antibodies can also be used to redirect effector lytic cells toward target cells.

Specific lysis of target cells is also a feature of certain aberrant physiological processes. Self-reactive T lymphocytes and antibodies are involved in the destruction of cells in autoimmune disorders such as insulin-dependent (Type 1) diabetes mellitus and autoimmune hemolytic anemia. Graft-versus-host disease (GVDH) develops when immunocompetent lymphocytes are injected into an allogeneic recipient whose immune system is compromised, e.g., a patient who has had radiation exposure or who has leukemia, immunodeficiency disease, or an autoimmune anemia and who is a recipient of an allogeneic bone marrow transplant. The grafted lymphocytes attack the host, whose immunocompromised state prevents an adequate immune response against the graft.

The cytolytic activity of $CD8^+$ T cells has been commonly determined by the $^{51}$Chromium ($^{51}$Cr) release assay. The standard $^{51}$Cr release assay has a number of disadvantages that include high spontaneous release, influence of $^{51}$Cr upon the effector cell population, problems with labeling certain cell types, low sensitivity, and health risks associated with gamma irradiation. Assays such as the modified enzyme linked immuno-assay (ELISPOT), which detects the secretion of cytokines following antigenic stimulation, and the use of tetrameric MHC class I complexes have afforded greater sensitivity in the detection of antigen specific $CD8^+$ T cells.

Non-radioactive alternatives to the standard cytotoxic assays have included detection of released intracellular enzymes, calorimetric assays or detailed preparation of reporter cell lines. In addition, assays that employ the use of flow cytometry by the detection of fluorescent dyes for either lymphocyte-target conjugate formation or cytolytic activity have been described. Flow cytometric cytotoxicity assays generally involve the measurement of a fluorochrome released from, or remaining in, pre-labeled effector cells or targets, simultaneously or exclusively. Ideally, these labels should not change the morphology or function of the labeled cells. However, some of the fluorochromes that have been proposed label target cells poorly, require complex manipulations of light scatter properties to discriminate the viable cell population or have a higher spontaneous release compared to standard $^{51}$Cr release. In addition, fluorometric techniques which rely on the incorporation of a nucleic acid stain such as propidium iodide, do not account for active phagocytic cells that can take up dead cells in vitro. As a consequence, none of these proposed assays have gained acceptance, or replaced the $^{51}$Cr release assay, which remains in widespread use.

To improve the study of in vitro cytolytic function of lytic agents such as cytolytic cells and antibodies, there is a need for a reliable assay that analyzes subpopulations, eliminates the requirement for potentially hazardous radioactive isotopes, offers increased sensitivity, utilizes an efficient label that is detected easily with low spontaneous release and is reproducible. The present invention addresses this need.

Literature

Lebow et al. (1986) *Nat. Immun. Cell Growth Regul.* 5 :221–237; Cavarec et al. (1990) *J. Immunol. Methods* 130 :251–261; Lebow and Bonavida (1990) *Proc. Natl. Acad. Sci. USA* 87:6063–6067; Callewaert et al. (1991) *Cytometry* 12 :666–676; Radcliff et al. (1991) *J. Immunol. Methods* 139 :281–292; Vitale et al. (1992) *J. Immunol. Methods* 149 :189–196; Radosevic et al. (1993) *J. Immunol. Methods* 135 :81–89; VanGraft et al. (1993) *Cytometry* 14 :257–264; King and Radicchi-Mastroianni (1996) *Cytometry* 24: 368–373; Zamai et al. (1998) *Cytometry* 32 :280–285; Shau and Dawson (1985) *J. Immunol.* 135 :137–140; Larsson and Nygren (1989) *Anticancer Res.* 9: 1111–1119; Chang et al. (1993) *J. Immunol. Methods* 166 :45–54; Hatam et al. (1994) *Cytometry* 16: 59–68; Karawajew et al. (1994) *J. Immunol. Methods* 177:119–130; Papa and Valentini (1994) *Methods Cell Bio.* 42: 193–207; Papadopoulos et al. (1994) *J. Immunol. Methods* 177:101–111; Flieger et al. (1995) *J. Immunol Methods* 180: 1–13; Johann et al. (1995) *J. Immunol Methods* 185 :209–216; Mattis et al. (1997) *J. Immunol. Methods* 204:135–142; Chang et al. (1998) *J. Immunol. Methods* 211 :51–63; Aubry et al. (1999) *Cytometry* 37 :197–204; Goldberg et al. (1999) *J. Immul Methods* 224 :1–9; Nociari et al. (1998) *J. Immunol. Methods* 213 :157–167; Slezak and Horan (1989) *J. Immunol. Methods* 117 :205–214; Radosevic et al. (1990) *J. Immul. Methods* 135 :81–89; Mattis et al. (1997) *J. Immunol. Methods* 204 :135–142;

Schafer et al. (1997) *J. Immul. Methods* 204 :89–84; Flieger et al. (1999) *Hybridoma* 18 :63–68; Beavis and Pennline (1994) *J. Immunol. Methods* 170 :57–65; Ford et al. (1996) *J. Surg. Res.* 62 :23–28; Garton and Schoenwolf (1996) *Anatomical Record* 244:112–117; Hasbold et al. (1998) *Immunol. Cell Biol.* 77 :516–522; Parish (1999) *Immunol Cell Biol.* 77: 499–508; Song et al. (1999) *Transplantation* 68 :297–299; Renno et al. (1999) *J. Immunol.* 162 :6312–6315.

SUMMARY OF THE INVENTION

The present invention provides methods of detecting specific lysis of a cell by a lytic agent. The methods generally involve contacting a labeled target cell with a lytic agent; and detecting fluorescence in the target cell. The target cells are labeled with two fluorescent labels: a fluorescent label that labels the plasma membrane; and a fluorescent label that labels the cytosol. Release of the cytosolic label from the target cell indicates that the target cell has been lysed. The invention further provides methods of detecting the presence in a sample of a cell that specifically lyses a target cell. The invention further provides methods of detecting the presence in a sample of an antibody that specifically lyses a target cell. The methods are useful in a variety of applications.

DEFINITIONS

Figure 1A:
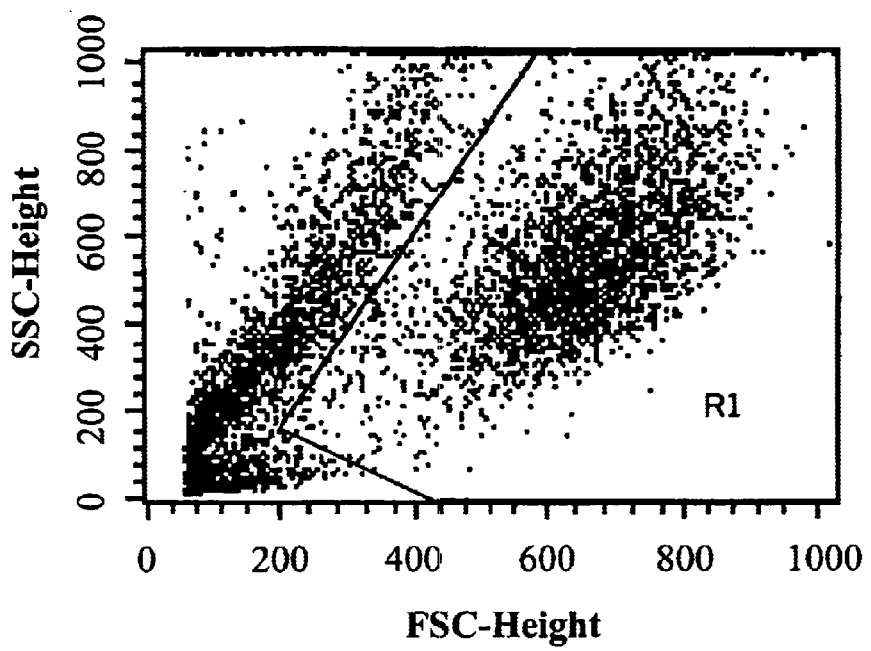
FIGS. 1A–D depict staining of cells with PKH-26 and CFSE, alone and in combination.
Figure 1B:
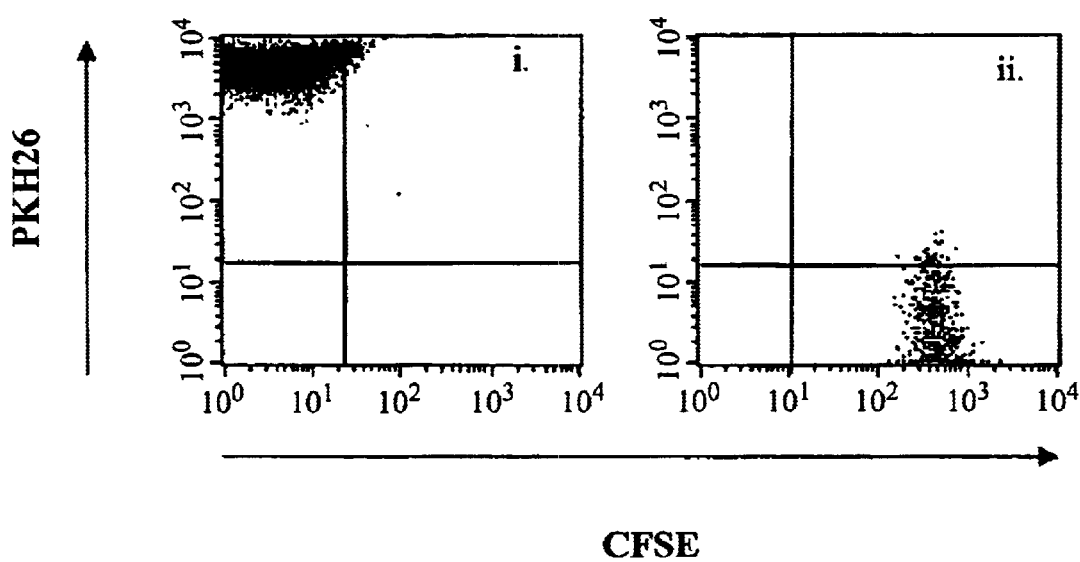

As used herein, the term "specific lysis" refers to lysis of a target cell based on the expression on its cell surface of a particular protein, peptide, glycoprotein, glycolipid, or lipoprotein. Specific lysis can be readily distinguished from non-specific lysis through the use of appropriate controls, e.g., a control cell (e.g., a cell of the same cell type, or a cell of same cell line) that does not express on its cell surface the same protein, peptide, glycoprotein, glycolipid, or lipoprotein that is the basis for specific lysis of the target cell.

The term "binds specifically," in the context of antibody binding, refers to high avidity and/or high affinity binding of an antibody to a specific polypeptide e.g., an epitope of a polypeptide. Antibody binding to an epitope on a specific polypeptide is preferably stronger than binding of the same antibody to any other epitope, particularly those which may be present in molecules in association with, or in the same sample, as the specific polypeptide of interest, e.g., binds more strongly to a specific epitope than to a different epitope so that by adjusting binding conditions the antibody binds almost exclusively to the specific epitope and not to any other epitope, and not to any other polypeptide which does not comprise the epitope.

Antibodies which bind specifically to a given polypeptide (or epitope) may be capable of binding other polypeptides at a weak, yet detectable, level (e.g., 10% or less of the binding shown to the polypeptide). Such weak binding, or background binding, is readily discernible from the specific antibody binding to the compound or polypeptide of interest, e.g. by use of appropriate controls. In general, antibodies which bind to a specific polypeptide with a binding affinity of $10^{-7}$ M or more, generally $10^{-8}$ M or more (e.g., $10^{-9}$ M, $10^{-10}$ M, $10^{-11}$ M, etc.) are said to bind specifically to the specific polypeptide. In general, an antibody with a binding affinity of $10^{-6}$ M or less is not considered "specific."

The term "binds specifically" in the context of an antigen-specific CD8$^+$ T lymphocyte refers to binding of the CD8$^+$ T cell to a particular peptide presented in a class I MHC molecule on a target cell, but not substantially to a different peptide presented in a class I MHC molecule on a target cell. The term "binds specifically" in the context of an antigen-specific CD4$^+$ T lymphocyte refers to binding of the CD4$^+$ T cell to a particular peptide presented in a class II MHC molecule on a target cell, but not substantially to a different peptide presented in a class II MHC molecule on a target cell.

The term "fluorescence" is well known in the art. In the context of a fluorescent dye, the term refers to a dye that can be excited at one wavelength of light following which it will emit light at another wavelength. Excitation generally occurs at a wavelength in the range of from about 250 to 750 nm. Emitted wavelengths are generally in the range of from about 200 nm to about 300 nm, from about 300 nm to about 400 nm, from about 380 nm to about 400 nm, from about 400 nm to about 430 nm, from about 430 nm to about 500 nm, from about 500 nm to about 560 nm, from about 560 nm to about 620 nm, from about 620 nm to about 700 nm, from about 700 nm to about 1.5 μm, from about 1.5 μm to about 20 μm, or from about 20 μm to about 1000 μm.

A fluorescent dye that is "distinguishable" from another fluorescent dye using standard detection methods and devices (e.g., flow cytometry devices), refers to the fact that the spectral properties of the two fluorescent dyes being compared are detectably different from one another, e.g., the emission of a given fluorescent dye differs from the emission of a second fluorescent dye by at least about 10 nm to about 15 nm, from about 15 nm to about 20 nm, from about 20 nm to about 25 nm, from about 25 nm to about 30 nm, from about 30 nm to about 35 nm, from about 35 nm to about 40 nm, from about 40 nm to about 45 nm, from about 45 nm to about 50 nm, from about 50 nm to about 55 nm, from about 55 nm to about 60 nm, from about 60 nm to about 65 nm, from about 65 nm to about 70 nm, from about 70 nm to about 75 nm, from about 75 nm to about 80 nm, from about 80 nm to about 85 nm, from about 85 nm to about 90 nm, from about 90 nm to about 95 nm, from about 95 nm to about 100 nm, from about 100 nm to about 120 nm, from about 120 nm to about 140 nm, from about 140 nm to about 160 nm, from about 160 nm to about 180 nm, or from about 180 nm to about 200 nm, or more.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell population, such as tumor cells, peripheral blood mononuclear cells (PBMC), lymphocytes, and the like. The term "biological sample" encompasses a clinical sample, and also includes cells in culture, cell supernatants, tissue samples, organs, bone marrow, and the like.

As used herein, the terms "determining" and "detecting" encompass qualitative and quantitative detection, and as such includes "measuring" and equivalent terms.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The terms "individual," "host," "subject," and "patient," used interchangeably herein, refer to a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a fluorescent dye" includes a plurality of such dyes and reference to "the target cell" includes reference to one or more target cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods for detecting and/or measuring specific lysis of a target cell; and methods for detecting in a sample the presence of and/or the number of cells having lytic activity toward a target cell. The methods generally involve labeling a target cell with two fluorescent labels: a fluorescent label that labels the plasma membrane; and a fluorescent label that labels the cytosol. The spectral properties of the cytosol-labeling fluorescent dye and the plasma membrane-labeling dye are distinguishable from one another using standard detection methods and devices. Release of the cytosolic label from the target cell indicates that the target cell has been lysed. The invention is useful in a variety of applications, e.g., in methods to determine tissue compatibility; in methods to determine the presence and/or extent of a graft-versus-host reaction; in methods to detect the presence of cytotoxic T lymphocytes reactive with self cell, with tumor cells, or with pathogen-infected cells; in methods to detect the presence of autoantibody reactive with a self target cell; and in methods of measuring an immune response to an antigen. Such methods are useful in diagnostic assays, e.g., to assist in making an initial diagnosis of a disease; in diagnostic assays to evaluate the efficacy of a treatment protocol; and in vaccine testing and evaluation.

The present invention avoids the disadvantages of methods that use radioactive labels such as $^{51}$Cr, such as problems with labeling certain cell types, low sensitivity, health risks associated with using radioactivity, and a high level of spontaneous release of label. The instant methods allow labeling of virtually any cell type. The label provides an easily detectable signal of high sensitivity that can be detected using simple detection methods. Unlike methods involving $^{51}$Cr labeling, in which populations of cells were analyzed, the instant methods allow analysis of specific cell lysis on an individual cell. In addition, unlike previous assays involving labeling cells with a single fluorescent dye, the present invention involves labeling target cells with two fluorescent dyes: one that labels the cytosol, and one that labels the plasma membrane. Labeling the target cell with both a cytosol-labeling fluorescent dye and a plasma membrane-labeling fluorescent dye is advantageous because the only cells that are labeled are viable cells, thereby avoiding the need for use of a dye to detect non-viable cells (e.g., dead cells or cells undergoing apoptosis) such as propidium iodide. Furthermore, in the instant methods, the label is released from a lysed cell quickly and uniformly, and lysed cells are no longer fluorescent.

Methods of Detecting Specific Lysis of a Target Cell

The present invention provides methods of detecting specific lysis of a target cell. The methods generally involve contacting a labeled target cell with a lytic agent, and detecting a reduction in fluorescence in the labeled target cell. Target cells are labeled with two fluorescent labels: a fluorescent label that labels the plasma membrane (a "plasma membrane-labeling fluorescent dye"); and a fluorescent label that labels the cytosol (a "cytosol-labeling fluorescent dye"). Release of the cytosolic label from the target cell indicates that the target cell has been lysed. Specificity is determined by providing suitable controls. 1 many embodiments, the methods are performed in vitro. In other embodiments, the methods are performed in vivo.

In some embodiments, the invention provides methods that involve contacting a lytic agent with two or more different types of target cells, in which each different target cell is labeled in such a way that allows it to be distinguished from the other target cell(s). These methods are advantageous because, in a single reaction mixture, a single lytic agent can be contacted with multiple target cells. If one type of target cell is lysed and a second type of target cell is not lysed, the two types of target cells can be distinguished from one another. It is advantageous to include multiple (e.g., two or more) different types of target cells in a single reaction mixture together with a lytic agent because it reduces the amount of time it takes to conduct the assays (i.e., less time is required to assay two or more different target cells simultaneously than would be required to assay individually); it reduces or eliminates the variability that might occur if each target cell were individually contacted with the lytic agent and assayed individually; and provides an internal 'intra-assay' control for specific lysis of a target cell.

An example of this method is the inclusion in a single reaction mixture of a lytic agent, and, as target cells: (1) a target cell that is being tested for whether it will or will not be lysed by the lytic agent; and (2) a control target cell that is not expected to by lysed by the lytic agent. In this example, a third control target cell that could be included is a positive control target cell, i.e., a target cell that is expected to be lysed by the lytic agent. Each target cell is labeled differently, such that the identity of the lysed and unlysed target cells are known.

Another example of this method is the inclusion in a single reaction mixture of a lytic agent and, as target cells: (1) a target cell from a first individual; and (2) a target cell from a second individual. In this example, control cells (as described in the preceding paragraph), as well as target cells from additional individuals, can also be included. As an example, target cells from multiple individuals who are potential organ donors are mixed with cells from a prospective organ recipient in a single reaction mixture. In this example, the prospective recipient's cells are being tested for lytic toward the potential donors' cells. Each potential donor's cells are labeled such that they can be distinguished from all other donors in the reaction mix. The best match between the donor and recipient is identified by determining which of the potential donor's cells are not lysed.

In some embodiments, the invention provides methods for detecting specific cell lysis where at least two different target cells are labeled with at least two different plasma membrane-labeling fluorescent dyes. These methods generally involve (a) contacting a lytic agent with (i) a first target cell labeled with a first plasma membrane-labeling fluorescent dye and a cytosol-labeling fluorescent dye and (ii) at least a second target cell labeled with a second plasma membrane-labeling fluorescent dye and the cytosol-labeling fluorescent dye; and (b) determining the amount of fluorescent label remaining in the first and at least the second target cell. The method may further include the step of relating the plasma membrane-labeling fluorescent dye in the unlysed target cell to the identity of the unlysed target cell.

A reduction in the amount of the cytosol-labeling fluorescent dye in a target cell indicates that the target cell is lysed by the lytic agent. The at least two different plasma membrane-labeling fluorescent dyes are distinguishable from one another by flow cytometry or other device for detecting fluorescence. Because the at least two different plasma membrane-labeling fluorescent dyes are distinguishable from one another, if a first target cell labeled with a first plasma membrane-labeling fluorescent dye is lysed and a second target cell labeled with a second plasma membrane-labeling fluorescent dye is not lysed, the identities of the lysed and the unlysed cell are known. Thus, the different plasma membrane-labeling dyes serve as a code for the different target cells.

In other embodiments, the invention provides methods for detecting lysis where at least two different target cells are labeled with at least two different cytosol-labeling fluorescent dyes. These methods generally involve (a) contacting a lytic agent with (i) a first target cell labeled with a first cytosol-labeling fluorescent dye and a plasma membrane-labeling fluorescent dye and (ii) at least a second target cell labeled with a second cytosol-labeling fluorescent dye and the plasma membrane-labeling fluorescent dye; and (b) determining the amount of fluorescent label remaining in the first and at least the second target cell. The method may further include the step of relating the cytosol-labeling fluorescent dye in the unlysed target cell to the identity of the unlysed target cell.

A reduction in the amount of the cytosol-labeling fluorescent dye in a target cell indicates that the target cell is lysed by the lytic agent. The at least two different cytosol-labeling fluorescent dyes are distinguishable from one another by flow cytometry or other device for detecting fluorescence. Because the at least two different cytosol-labeling fluorescent dyes are distinguishable from one another, if a first target cell labeled with a first cytosol-labeling fluorescent dye is lysed and a second target cell labeled with a second cytosol-labeling fluorescent dye is not lysed, the identities of the lysed and the unlysed cell are known. Thus, the different cytosol-labeling dyes serve as a code for the different target cells.

In further embodiments, the invention provides for methods of detecting specific cell lysis, wherein a plurality of target cells is contacted with a lytic agent, and wherein a plurality of plasma membrane-labeling fluorescent dyes and a plurality of cytosol-labeling dyes is used to label the target cells. For example, a subset of target cells may be labeled in such a way that distinguishes the subset. An examples of a subset are control target cells, which subset in many embodiments includes at least two types of control cell.

These embodiments are useful in that more than one target cell or cell population can be analyzed simultaneously with a single lytic agent. Thus, these methods provide for contacting a plurality of target cells with a single lytic agent. For example, a test target cell and one or more different control target cells can be analyzed simultaneously with a single lytic agent. As another example, target cells from more than one individual can be analyzed simultaneously with a single lytic agent.

In some embodiments, the at least two different target cells include a first target cell that displays a peptide on its surface that is recognized by an lytic agent; and a second, control target cell lacking the peptide and/or a control target cell displaying a different peptide from the one displayed by the first target cell such that it is not recognized and lysed by the lytic agent.

In other embodiments, the at least two different cells include a first target cell from a patient, which first target cell is infected with an intracellular pathogen; and a second, control target cell that is not infected with the intracellular pathogen and/or a control target cell that is infected with an intracellular pathogen different from the one that the first target cell is infected with, such that the control target cell is not recognized and lysed by the lytic agent.

In still other embodiments, the at least two different target cells include a first target cell from a first individual; and at least a second target cell from at least a second individual. Multiple target cells (including control target cells) can be analyzed simultaneously with a single lytic agent.

As one non-limiting example, the target cell sample includes: a control target cell, a target cell from a first individual being tested for tissue compatibility, and a target cell from a second individual being tested for tissue compatibility. In this example, the target cell sample can further include target cells from additional individuals being tested for tissue compatibility. The target cell sample could thus include target cells from multiple potential plasma membrane/organ donors, each labeled with a different plasma membrane dye. The target cell sample, including appropriate controls, is then contacted with a lytic agent, which in this case could be a peripheral blood mononuclear cell sample from a prospective tissue/organ recipient, or a sample of $CD8^+$ cells from the prospective recipient. Thus, in one assay, the potential donor who presents the best tissue match with the prospective recipient is identified.

In many embodiments, the subject methods are performed in vitro, e.g., target cells are labeled in vitro, and contacted with lytic agent in vitro. In other embodiments, the subject methods are performed in vivo. In these embodiments, the cells are labeled in vitro, and subsequently introduced into an animal, e.g., an experimental non-human animal, i.e., the labeled target cell is contacted with the lytic agent in vivo. In some of these embodiments, the lytic agent is present in the experimental animal (e.g., the lytic agent is an endogenous cell or antibody having lytic activity toward the target cell); and in other embodiments, the lytic agent is introduced into the experimental animal. Where the subject method is performed in vivo, detection of cell lysis can occur in vitro, e.g., the target cells (and the lytic agent) can be removed from the animal, and subjected to flow cytometry to detect specific lysis. Alternatively, an in vivo imaging technique can be used to detect specific cell lysis in vivo.

Fluorescent Labels

Target cells are labeled with two fluorescent labels: a fluorescent label that labels the plasma membrane; and a fluorescent label that labels the cytosol. The use of a label for the plasma membrane facilitates analysis of the cells, as it allows discrimination between cells that have been lysed, and cells that have died due to causes unrelated to specific cell lysis.

Fluorescent dyes that label the plasma membrane and are suitable for use in the instant methods are non-cytotoxic, have no effect on biological activities of the cell, yield intense staining with a high signal:noise ratio, label any cell type, provide for uniform labeling of the plasma membrane, and are compatible with existing detection equipment and standard fluorescent filters. Fluorescent labels that label the plasma membrane include lipid-associated fluorescent labels, including, but not limited to, PKH-26, PKH-67 and long chain dialkylcarbocyanines such as 3,3'-dioctadecyloxacarbocyanine perchlorate (DiO), 1,1'-dioctadecyl-3,3,3',3'-tetramethylindocarbocyanine perchlorate (DiI), 1,1'-dioctadecyl-3,3,3',3'-tetramethylindodicarbocyanine perchlorate (DiD), 4-(4-(dihexadecylamino)styryl)-N-methylpyridinium iodide (DiA); and 1,1'-dioctadecyl-3,3,3',3'-tetramethylindotricarbocyanine iodide (DiR). Also of interest are variants of DiO, DiI, DiD, DiA, and DiR, including, but not limited to, variants which have shorter alkyl substituents, e.g., $C_{12}$, and $C_{16}$ alkyl substituents (e.g., $DiIC_{12}$, $DiIC_{16}$, $DiOC_{16}$, and the like; variants which have diunsaturated alkyl substituents, e.g., $\Delta^{9,12}$-C18 alkyl substituents; variants having phenyl substituents attached to the indoline rings of DiI; sulfonated derivatives of DiI and DiO; and the like. Many such dyes are commercially available. Sigma (St. Louis, Mo.) and Molecular Probes (Eugene, Oreg.) are examples of commercial sources of such dyes.

Fluorescent labels that label the cytosol that are useful in the methods of the present invention include fluorescent labels that permeate the plasma membrane and bind to intracellular proteins in the cytosol. Suitable fluorescent dyes are those that: (1) are spontaneously released from the cytosol at a very low rate; label virtually any cell type; are released from a lysed cell very rapidly, and in one step; do not alter the morphological or biological characteristics of the cell; label the cells such that they are readily detectable, e.g., labeled cells are brightly fluorescent; and are detectable using existing equipment and standard fluorescent filters.

Fluorescent dyes that label the cytosol that are useful in the methods of the present invention are those that are spontaneously released from a cell at a very low rate, e.g., less than about 15%, less than about 10%, less than about 8%, less than about 5%, or less than about 2% spontaneous release occurs during an incubation in standard culture conditions (e.g., 37° C., 5% $CO_2$) of from about 2 hours to about 4 hours, from about 4 hours to about 8 hours, from about 8 hours to about 12 hours, from about 12 hours to about 24 hours, from about 24 hours to about 36 hours, or from about 36 hours to about 48 hours.

Cytosol-labeling fluorescent dyes that are useful in the methods of the invention label virtually any cell, including, but not limited to, animal cells, including mammalian cells; plant cells; yeast cells; fungal cells; protozoal cells; and the like.

Fluorescent, cytosol-labeling dyes that are suitable for use in the present invention are released rapidly from a lysed cell, e.g., at least about 80%, at least about 85%, at least about 90%, at least about 95%, at least about 98%, or more, of the fluorescent dye is released from a lysed cell in about 10 seconds, in about 5 seconds, in about 2 seconds, in about 1 second, or in about 100 milliseconds, or less, of lysis of the cell.

In many embodiments of interest, a cytosol-labeling fluorescent label is an uncharged derivative of fluorescein that is cleaved in the cytosol to produce a charged form that is highly fluorescent. For example, amine-reactive carboxyfluorescein succinimidyl esters that are cleaved by intracellular esterases to yield highly fluorescent amine-reactive fluorophores are suitable. Suitable cytosol-labeling fluorescent dyes include, but are not limited to, 5-(-6)-carboxyfluorescein diacetate succinimidyl ester (CFSE); CMTMR (5-(6) (((4-chloromethly) benzoyl) amino) tetramethylrhodamine); CMAC (7-amino-4-chloromethylcoumarin); and a SNARF® fluorescent dye. Such dyes are commercially available, e.g., from Molecular Probes (Eugene, Oreg.). In a particular embodiment of interest, the cytosol-labeling fluorescent dye is CFSE.

If desired, target cells and/or effector cells (i.e., cells having lytic activity toward a target cell) can further be labeled with additional labels, including, but not limited to, a detectably labeled antibody specific for a particular cell surface marker; a dye for detecting non-viable cells (e.g., propidium iodide); and the like. Such labeling may be performed to assist in identifying the target and/or effector cell populations or to gate out non-viable cells.

Lytic Agents

Lytic agents include any agent that effects, directly or indirectly, specific lysis of a target cell. Lytic agents include, but are not limited to, antibodies specific for a cell surface marker of a target cell; "effector cells," including antigen-specific effector cells and non-antigen-specific effector cells, including, but not limited to, $CD8^+$ T lymphocytes; $CD4^+$ T lymphocytes; NK cells; NKT cells; LAK cells; and combinations of specific antibody and non-specific effector cells, e.g. an antibody that is specific for a target cell surface molecule, and an effector cell that bears a cell surface Fc receptor, including, but not limited to, NK cells, macrophages, eosinophils, monocytes, and neutrophils.

Target Cells

Target cells are any cells that are specifically lysed by a lytic agent, e.g., a lytic cell or a specific antibody. In many embodiments, a target cell is lysed by a lytic agent that specifically recognizes and binds to a protein, peptide, glycoprotein, glycolipid, or lipoprotein on the surface of the target cell.

In many embodiments, target cells display an antigenic peptide on their surface in a Class I major histocompatibility complex (MHC) molecule. In many of these embodiments, the target cell is recognized and lysed by the lytic cell in an antigen-specific manner, i.e., the lytic cell recognizes an antigenic peptide presented by the class I MHC molecule and lyses the target cell. In these embodiments, the lytic cell is generally a $CD8^+$ T lymphocyte.

In other embodiments, the target cell displays on its cell surface a protein, peptide, glycoprotein, glycolipid, or lipoprotein that is specifically recognized and bound by a lytic agent, such as a specific antibody.

In some embodiments, a target cell is a cell line that is charged with a peptide to which a lytic cell is specific.

Antigenic peptides can be bound to the antigen binding site of the MHC molecule or to the amino-terminus of either an MHC class I chain or a $\beta_2$ microglobulin. Binding, or "loading" of the antigenic peptide to the MHC molecule can be carried out actively or passively. The antigenic peptide can be covalently bound to the chimeric protein. Optionally, a peptide tether can be used to link an antigenic peptide to $\beta_2$ microglobulin. Crystallographic analyses of multiple class I MHC molecules indicate that the amino terminus of $\beta_2$ microglobulin is very close, approximately 20.5 Å away, from the carboxyl terminus of the antigenic peptide resident in the MHC peptide binding groove. Thus, using a relatively short linker sequence, approximately 13 amino acids in length, one can tether a peptide to the amino terminus of $\beta_2$ microglobulin. If the sequence is appropriate, that peptide will bind to the MHC binding groove.

In other embodiments, a target cell is a naturally-occurring cell in a biological sample. Biological samples containing a target cell include graft tissue; a biological sample which is being tested for the presence of a target infected with an intracellular pathogen; a biological sample that contains (or which is being tested for the presence of) a target cell that is lysed by an autoimmune cell; a biological sample that contains (or which is being tested for the presence of) a target cell that is lysed by a foreign (non-host) cell (e.g., a target of a graft-versus-host disease response); a biological sample that is being tested for tissue compatibility with a prospective tissue/organ recipient; and the like.

Biological samples that are suitable for use depend on various factors, including the nature of the specific cell lysis being detected. For example, a blood sample may be used to determine histocompatibility between potential donors and a prospective recipient. Blood samples include whole blood samples, peripheral blood mononuclear cells, blood cells enriched for particular sub-populations, etc.

Biological samples containing a naturally-occurring target cell include a cell in graft tissue or organ (e.g., tissue or organ that has been grafted or is to be grafted into an individual), including, but not limited to, bone marrow, skin, liver, pancreas, kidney, lung, heart, pancreatic islet cells, cord blood, whole blood, blood fractions, and the like.

Biological sources of target cells also include a biological sample containing a cell that is infected with an intracellular pathogen, including, but not limited to, viruses (e.g., CMV HIV), bacteria (e.g., Listeria, Mycobacteria, Salmonella (e.g., *S. typhi*) enteropathogenic Escherichia coli (EPEC), enterohaemorrhagic *Escherichia coli* (EHEC), Yersinia, Shigella, Chlamydia, Chlamydophila, Staphylococcus, Legionella), protozoa (e.g., Taxoplasma), fungi, and intracellular parasites (e.g., Plasmodium (e.g., *P. vivax, P. falciparum, P. ovale*, and *P. malariae*).

Labeling Target Cells

Target cells are labeled using any known method, including, e.g., the method described in Example 1. Generally, cells are labeled in a medium containing a buffer, and are labeled at room temperature (e.g., from about 19° C. to about 23° C.), although other temperatures, e.g., physiological temperatures (e.g., 37° C.), can be used. Generally, incubation of the dye with the target cell for a period of from about 15 seconds to about 2 minutes, although longer incubation periods may also be used. The dyes are readily taken up by the cells. Labeling with the cytosol-labeling fluorescent dye is stopped by addition of excess protein, e.g., albumin, fetal bovine serum, and the like. One or more washing steps can be performed after the cells are labeled. Labeled cells can be maintained at 4° C. for a period of time (e.g., 2 hours, 4 hours, 8 hours, 12 hours, 24 hours, 48 hours, or longer) before being analyzed, if desired. Labeled cells can be further processed for analysis, e.g., by flow cytometry. For example, labeled cells can be treated with 1% paraformaldehyde.

Detecting Cell Lysis

Target cell lysis is detected by detecting and/or measuring cytosol-labeling fluorescent dye remaining in the cytosol of the target cell. Fluorescence is detected using a flow cytometry device or a fluorescent microscope.

In some embodiments, target cell lysis is detected using a flow cytometry device. Flow cytometry devices and protocols are well known in the art, and have been amply described in numerous publications. See, e.g., *Flow Cytometry and Sorting*, $2^{nd}$ ed. (1990) M. R. Melamed et al., eds. Wiley-Liss; *Flow Cytometry and Cell Sorting*, $2^{nd}$ ed. (2000) A. Radbruch, Springer-Verlag; and *In Living Color: Protocols in Flow Cytometry and Cell Sorting* (2000) Diamond and Demaggio, eds, Springer-Verlag. Flow cytometry methods are also described in U.S. Pat. Nos. 5,968,738 and 5,804,387; the disclosures of which are herein incorporated by reference. In certain embodiments, a flow cytometer that is capable of multicolor analyses (e.g., 2, 4, 6, 8, or more different colors) is used.

Where fluorescence is detected using a flow cytometry device, lysis is detected by detecting and/or measuring cytosol-labeling fluorescent dye remaining in the cytosol of the cell. A reduction in the amount of fluorescence indicates that cell lysis has occurred. For example, target cell lysis can be expressed as 100%-% survival, where percent survival= (mean percent labeled cells/mean percent spontaneous release of dye)×100.

Where the source of target cells is an organ or other solid tissue, and the detection method is flow cytometry, the target cells are generally are generally released from the organ or solid tissue using standard methods, e.g. collagenase treatment.

Methods of Detecting Cells Having Lytic Activity

The present invention further provides methods of detecting the presence of, or determining the number of, cells in a sample which have lytic activity toward a target cell. A cell that has lytic activity toward a target cell is referred to herein as an "effector cell." The methods generally involve labeling a target cell, as described above; contacting the labeled target cell with a biological sample that is being tested for the presence of a cell having lytic activity toward the target cell; and detecting specific lysis of the target cell. In many embodiments, the methods are performed in vitro.

Specific lysis of the target cell indicates the presence in the sample of a lytic cell that is specific for the target cell. Whether lysis is specific can be determined by including appropriate controls. For example, if the target cell is a cell line that is loaded with a peptide antigen, a control sample includes a cell of the same cell line not loaded with the peptide, or loaded with a different, non-cross-reactive peptide.

In some embodiments, a biological sample is tested for the presence of a cell having lytic activity toward an autologous cell, e.g., an autoreactive cytotoxic T lymphocyte (CTL). In these embodiments, target cells include cells in a biological sample from an individual being tested for the presence of autoreactive CTLs; and a cell loaded with a peptide known to be recognized by an autoreactive CTL. Target cells are labeled as described above, then contacted with a biological sample from the individual. Specific lysis of the target cell indicates the presence in the sample from the individual of autoreactive CTLs. Control target cells include a cell line not loaded with the peptide; or a biological sample from the individual that is known not to contain cells of the cell type recognized by a particular autoreactive CTL. For example, where the autoreactive CTL recognizes a pancreatic cell, a control cell is a cell from the same individual that is other than a pancreatic cell, e.g., a liver cell; and the like. These methods are useful to diagnose an autoimmune disorder that is due to the presence of autoreactive CTLs, including, but not limited to, Type 1 diabetes, autoimmune hepatitis, systemic lupus erythematosis; scleroderma; autoimmune thyroiditis; rheumatoid arthritis; myocarditis; and inflammatory bowel disease.

These methods are also useful in assessing the efficacy of a treatment method for an autoimmune disorder that is due to the presence of autoreactive CTLs. For example, a decrease in the number of autoreactive CTLs following a particular treatment protocol indicates efficacy of treatment.

In some embodiments, the methods provide for detection in a biological sample of a cell that mediates graft-versus-host disease (GVHD). GVHD is caused by donor T-cells reacting against systemically distributed incompatible host antigens, causing powerful inflammation. In GVHD, mature donor T-cells that recognize differences between donor and host become systemically activated. Frequently, the host is immunocompromised, e.g., due to immunosuppressive chemotherapy, or cancer chemotherapy. In these embodiments, the biological sample includes graft tissue that is about to be engrafted into a host (e.g., bone marrow cells); as well as graft tissue that has already been introduced into a host. Target cells are labeled as described above, and are generally host cells. These methods are useful for diagnosing GVHD, as well as for assessing the efficacy of a treatment for GVHD.

In other embodiments, the methods provide for detection in a biological sample of a cell that has lytic activity toward a tumor cell. In these embodiments, the target cell is a tumor cell from an individual, and is labeled as described above. Cells from the same individual that have lytic activity toward the labeled tumor cells are detected by contacting the labeled tumor cells with cells from the individual. The methods are useful to assess the extent of a host CTL response to a tumor in the host, as well as to assess the efficacy of a treatment protocol to boost a host's CTL response to a tumor.

The methods are also useful to detect the presence in an individual of tumor cells that are refractory to lysis by autologous CTLs. In these embodiments, the labeled target tumor cells are contacted with autologous CTLs that specifically lyse the labeled tumor cells. The presence of labeled tumor cells that are not lysed by tumor-specific autologous CTLs indicates the presence in the individual of tumor cells that are refractory to lysis by autologous CTL. The presence of such cell in the individual could suggest the need to modify a treatment protocol, e.g., to boost the host's immune response to such refractory cells.

In other embodiments, the methods provide for detection in a biological sample of a cell that has lytic activity toward a pathogen-infected cell. In these embodiments, the target cell includes a cell line that is infected in in vitro cell culture with the pathogen; a cell from an individual that is infected in in vitro cell culture with the pathogen; and a cell from an individual that is known to be infected with a given pathogen. The target cell is labeled, and contacted with a biological sample being tested for the presence of a cell that has lytic activity toward a pathogen-infected cell. Lysis of the labeled target cell indicates the presence in the sample of such cells. Suitable controls include target cells infected with an unrelated pathogen.

In other embodiments, the methods provide for detection of antibody-dependent cell-mediated cytotoxicity (ADCC). In these embodiments, target cells are typically pathogen-infected cells or cancerous cells. Lytic cells include, but are not limited to, NK cells, macrophages, eosinophils, monocytes, and neutrophils. A target cell is labeled as described above, and contacted with a sample comprising antibody specific for the target cell; and a sample being tested for the presence of lytic cells bearing on their cell surface an Fc receptor. Specific lysis of the target cell indicates the presence of such lytic cells. Suitable controls include labeled target cells not bound with specific antibody, e.g., labeled target cells contacted with a non-specific antibody.

Methods of Detecting Antibody Having Lytic Activity

The invention also provides methods of detecting the presence in a biological sample of an antibody having lytic activity toward a target cell. Biological samples to be tested for the presence of and/or an amount of, antibody having lytic activity toward a target cell include serum. In some embodiments, components of the complement system are added to the test sample, which comprises the labeled target cells and the sample being tested for the presence of lytic antibody. The biological source of the target cells depends in part upon the nature of the lytic antibody being tested for. For example, where the lytic antibody is one that mediates lysis of red blood cells, sources of target cells include red blood cells.

Uses

The methods of the invention are useful in a variety of diagnostic and screening methods. Diagnostic methods include methods of diagnosing a disease; methods for testing a treatment protocol that is being developed; and methods for testing the efficacy of a treatment protocol. Screening methods include methods of identifying an agent that increases or decreases specific cell lysis. Screening methods are described in more detail below.

The methods of the invention are useful in a variety of diagnostic applications, e.g., in methods to determine tissue compatibility; in methods to determine the presence and/or extent of graft-versus-host reaction; in methods to detect the presence of and/or determine the number of CTL in an individual that have lytic activity toward an autologous tumor cell; in methods to detect the presence of and/or determine the number of tumor cells in a biological sample that are not lysed by autologous CTLs; in methods to detect the presence of and/or determine the number of autoreactive CTLs in a biological sample; in methods to detect the presence of and/or determine the number of CTLs in a biological sample that are reactive toward a pathogen-infected cell; and in methods to detect the presence of and/or measure the amount of, antibody in a biological sample, which antibody has lytic activity toward a cell.

In determining tissue compatibility ("tissue typing") cells from a donor individual (e.g., a potential donor) are mixed with cells taken from a prospective recipient and labeled. Sources of donor cells include, but are not limited to, autologous (self), xenogeneic sources, an HLA-matched sibling, an unrelated HLA-matched individual, a cadaver, or cloned tissue. Often, blood cells from a potential donor are mixed with blood cells from a recipient. Using the methods of the invention, the presence of cells showing lytic activity toward recipient cells is detected by detecting the amount of cytosol-labeling fluorescent dye remaining in the labeled target population after mixing the labeled target population with the cells from the potential donor. Lack of specific lysis with a particular potential donor cell population indicates the suitability of the donor as a source of tissues (e.g., blood, organs, pancreatic cells, and the like) for that particular recipient.

In determining the presence and/or extent of GVHD, cells from tissue engrafted into a host are removed from the host and mixed with host cells. Host cells are labeled, as described above, and the presence of cells showing lytic activity toward host cells is detected by detecting the amount of cytosol-labeling fluorescent dye remaining in the labeled target population after mixing the labeled target population with the cells from the engrafted tissue.

In detecting the presence of and/or determining the number of CTLs in an individual that have lytic activity toward an autologous tumor cell, cancerous cells are removed from the individual, labeled as described above, and mixed with $CD8^+$ T lymphocytes from the individual. The presence of CTLs in the individual that have lytic activity toward the cancerous cells is detected by detecting the amount of cytosol-labeling fluorescent dye remaining in the labeled target tumor cell population after mixing the labeled target population with host CTLs. Such an analysis can be conducted following treatment of the patient with a cancer treatment protocol, to determine the efficacy of such treatment. Such an analysis is also useful to detect the presence in a population of tumor cells of tumor cells that are refractory to lysis by a patient's CTLs. Where tumor cells that are refractory to lysis by a patient's CTLs are detected, a change in treatment protocol may be indicated.

The methods of the invention are also useful in vaccine development, and in testing the efficacy of a vaccine protocol. For example, a vaccine comprising naturally occurring or synthetic components of a pathogenic organism is tested. After administering the vaccine to an individual, the individual is tested for the number of pathogen-specific CTLs (e.g., CTLs specific for one or more epitopes presented in the vaccine). Target cells include cells of a cell line that have been loaded with synthetic or naturally occurring peptides from a pathogenic organism; or cells from the individual that have been infected (e.g., in vitro) with the pathogen. Target cells are labeled as described above, and contacted in vitro with a biological cell sample from the individual, e.g., a blood sample. The presence of CTLs in the individual that have lytic activity toward the target cells is detected by detecting the amount of cytosol-labeling fluorescent dye remaining in the labeled target cell population after mixing the labeled target cells with host cells. Suitable controls include cells of a cell line not loaded with peptide; and cells from the host that have not been infected in vitro with the pathogen.

The methods are also useful to evaluate an immune response (innate, humoral, and cellular) to an antigen. After an individual is exposed to an antigen (e.g., by immunization or by accidental exposure), the immune response to the antigen can be determined by contacting a labeled target cell, which displays the antigen (or an epitope of the antigen) on its cell surface, with cells (e.g., whole blood cells, PBMC's, a sub-population of blood cells) from the individual, or with serum from the individual, and determining the extent of specific cell lysis. In some embodiments, cells displaying the antigen or epitope on their cell surface are a cell line loaded with peptide, such that the peptide is displayed in an MHC molecule. Such cells are useful to detect cells having specific lytic activity toward cells displaying the antigen.

Screening Methods

The present invention further provides methods of identifying agents that modulate specific lysis of a target cell. The methods generally involve a sample that includes a labeled target cell and a lytic agent with a test agent; and detecting fluorescence in the labeled target cell. The target cell is labeled as described above with a fluorescent dye that labels the plasma membrane, and a fluorescent dye that labels the cytosol. As used herein, the term "modulate" encompasses "increase" and "decrease."

A reduction in fluorescence in the labeled target cell, compared to a control sample, indicates that the agent increases specific cell lysis. Control samples do not contain the test agent. In some embodiments, a suitable control is a sample that includes a labeled target cell and a lytic agent that effects specific lysis of the target cell. In the control sample, the fluorescence decreases at a given rate. An increase in the rate of decrease of fluorescence in the sample that includes the test agent indicates that the test agent increases specific cell lysis. In other embodiments, a suitable control is a sample that includes a labeled target cell and a lytic agent that does not effect lysis of the target cell, or effects lysis of the target cell inefficiently. In the control sample, fluorescence does not decrease, or decreases at only a very low rate. An increase in the rate of decrease of fluorescence in the sample that includes the test agent indicates that the test agent increases specific cell lysis.

Agents of interest increase specific cell lysis by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more, when compared with a suitable control. Agents that increase specific cell lysis are of interest in applications such as treating cancer, treating intracellular pathogen infections, and the like.

A decrease in reduction of fluorescence in the labeled target cell, compared to a control sample, indicates that the agent reduces specific cell lysis. Control samples do not contain the test agent. In some embodiments, a suitable control includes a labeled target cell and a lytic cell that effects lysis of the target cell. In the control sample, fluorescence decreases at a given rate. A reduction in the rate of decrease of fluorescence in the sample that includes the test agent indicates that the test agent reduces specific cell lysis.

Agents of interest decrease specific cell lysis by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more, when compared with a suitable control. Agents that decrease specific cell lysis are of interest in applications such as treating certain autoimmune disorders, GVHD, and the like.

The terms "test agent," "candidate agent," "substance," and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Agents further encompass interfering RNA molecules, antibodies, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidation, etc. to produce structural analogs.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Target cells are labeled as described above. In some embodiments, the lytic agent is an effector cell, as described above. In some of these embodiments, the effector cell is not itself specific for a target cell; instead, specificity is imparted by an antibody specific for the target cell, and the effector cell has an Fc receptor on its cell surface (e.g., a macrophage, neutrophil, monocyte, NK cell, and the like), as described above. In other embodiments, the lytic agent is an antibody, as described above.

Typically, fluorescence is detected using flow cytometry. In some embodiments, the assays are adapted to a high through-put format.

Agents

The invention further provides agents identified using an assay method of the invention. As discussed above, agents that increase specific cell lysis are useful in treating cancer, in treating intracellular pathogen infections, and the like. Agents that decrease specific cell lysis are useful to treat GVHD, autoimmune disorders that involve specific cell lysis, graft rejection, and the like.

Formulations

In the subject methods, the active agent(s) may be administered to the host using any convenient means capable of resulting in the desired increase or decrease in specific cell lysis.

The agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one that provides up to about 1 $\mu$g to about 1,000 $\mu$g or about 10,000 $\mu$g of an agent that increases or decreases specific cell lysis can be administered in a single dose. Alternatively, a target dosage of an agent that increases or decreases specific cell lysis can be considered to be about in the range of about 0.1–1000 $\mu$M, about 0.5–500 $\mu$M, about 1–100 $\mu$M, or about 5–50 $\mu$M in a sample of host blood drawn within the first 24–48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that increases or decreases specific cell lysis is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrastemal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Treatment Methods

The present invention further provides methods of treating disorders related to specific cell lysis. The methods generally involve administering an effective amount of an active agent as described above.

Agents that decrease specific cell lysis are used to treat disorders associated with specific cell lysis that is deleterious to a host, including, but not limited to, GVHD, and autoimmune disorders involving lysis of "self" cells. An effective amount of an agent that decreases specific cell lysis is administered to an individual in need thereof. An effective amount is an amount that decreases specific cell lysis by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more, when compared with specific cell lysis that occurs in the absence of treatment with the active agent.

Individuals that are suitable for treatment include, but are not limited to, individuals who have been diagnosed with GVHD; individuals at risk of developing GVHD (e.g., due to being a graft recipient); individuals who have been diagnosed with an autoimmune disorder that results from destruction of cells due to specific cell lysis (e.g., Type 1 diabetes); individuals who show symptoms of graft rejection; individuals who are at risk of graft rejection; and the like.

Agents that increase specific cell lysis are used to treat disorders that are amenable to treatment with specific cell lysis, e.g., where the host has not mounted a CTL response or has mounted a CTL response that is inadequate to effectively control the disorder. Such disorders include, but are not limited to, cancer, infection with an intracellular pathogen, and the like. An effective amount of an agent that increases specific cell lysis is administered to an individual in need thereof. An effective amount is an amount that increases specific cell lysis by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more, when compared with specific cell lysis that occurs in the absence of treatment with the active agent.

Kits

The present invention further provides kits for use in practicing one or more of the above-described methods, where the subject kits include a fluorescent dye for labeling the plasma membrane; a fluorescent dye for labeling the cytosol. The dyes are present in a suitable storage medium, e.g., buffered solution, typically in a suitable container. In some embodiments, one or more antibodies specific for one or more cell surface markers are included. In some embodiments, at least one of the antibodies is detectably labeled.

In some embodiments, a subject kit includes a cytosol-labeling fluorescent dye, a first plasma membrane-labeling fluorescent dye, and at least a second plasma membrane-labeling fluorescent dye, which second plasma membrane-labeling fluorescent dye has spectral properties that are distinguishable from the first plasma membrane-labeling fluorescent dye. In some of these embodiments, the cytosol-labeling fluorescent dye is provided in a separate vial from the plasma membrane-labeling dyes.

In many embodiments, a plurality of plasma membrane-labeling dyes is provided, each of which has spectral properties that are distinguishable from those of the other plasma membrane-labeling dyes. In other embodiments, each of the plasma membrane-labeling dyes is provided pre-mixed separately with the cytosol-labeling dye.

In other embodiments, a subject kit a plasma membrane-labeling fluorescent dye, a first cytosol-labeling fluorescent dye, and at least a second cytosol-labeling fluorescent dye, which second cytosol-labeling fluorescent dye has spectral properties that are distinguishable from the first cytosol-labeling fluorescent dye. In some of these embodiments, the plasma membrane-labeling fluorescent dye is provided in a separate vial from the cytosol-labeling dyes. In many embodiments, a plurality of cytosol-labeling dyes is provided, each of which has spectral properties that are distinguishable from those of the other cytosol-labeling dyes. In other embodiments, each of the cytosol-labeling dyes is provided pre-mixed separately with the plasma membrane-labeling dye.

In other embodiments, a subject kit further includes target cells. In general, target cells are standard cell lines. Target cells are generally frozen. Target cells are stored in appropriate storage buffer, which may include one or more agents that preserve cell viability and reduce cell damage during thawing.

In still other embodiments, a subject kit further includes peptides that correspond to a particular intracellular pathogen or tumor-associated antigen.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disk, etc., on which the information has been recorded. Yet another means that may be present is a website address which may be used via the internet to access the information at a removed site. Any convenient means may be present in the kits.

Systems

The present invention further provides a system for detecting specific cell lysis. A subject system generally includes a plasma-labeling fluorescent dye; a cytosol-labeling fluorescent dye; a target cell; and a device for detecting fluorescence in a cell, e.g., a flow cytometer. A subject system may further include a lytic agent. A subject system may further include one or more additional dyes or other detectable markers, as described above. A subject system is used to perform a diagnostic or a screening method described herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Antigen-Specific Lysis of Target Cells Labeled with PKH-26 and CFSE

This example describes an assay termed "fluorometric assessment of T lymphocyte antigen-specific lysis" or FATAL, and compares this assay to the $^{51}$Cr release assay.

Materials and Methods

Generation of Effector Cells

To evaluate antigen specific CD8$^+$ T-cell effector activity, cytomegalovirus (CMV) specific CTLs were used as effector cells and B-lymphoblastoid cell lines (BCL) as target cells. Several CMV-pp65 peptide (495–503: NLVPMVATV; SEQ ID NO:1) specific semi-clones from an HLA-A*0201, CMV seropositive donor were generated as previously described (Wills et al. (1996) *J. Virol.* 70:7569–7579).

Preparation of Target Cell Populations

BCL were used as target cells in both the $^{51}$Cr release and FATAL assays. Both assays were performed with immortalized BCL from an HLA-A*0201 individual. The BCL were incubated with 10 μg/ml of the HLA-A*0201 restricted cytomegalovirus (CMV)-pp65 (495–503: NLVPMVATV; SEQ ID NO:1) peptide for 1 hour at 37° C. in 5% $CO_2$ prior to use in the assays. An HLA-A*0201 restricted HIV-Gag peptide (77–85: SLYNTVATL; SEQ ID NO:2) was used as a negative control. In addition, target BCL were incubated without peptide as background controls. Further experiments used BCL infected with recombinant vaccinia virus (rVV) overnight expressing CMV antigen (CMVpp65-rVV) or control vaccinia (Vaccinia Thymidine kinase negative, TK) (Therion Biologics, Cambridge, Mass.). To confirm HLA-A*0201 restricted specific lysis, HLA mismatched BCL were included in the assays. All target cells were washed once in PBS, centrifuged for 5 minutes at 400%g, the supernatant was discarded and cells were resuspended prior to use. (Biowhittaker, Walkersville, Md.). The cell number and viability were assessed by trypan blue exclusion (Biowhittaker). The antigen labeled target and control cells were subsequently used in the FATAL and $^{51}$Cr release cytotoxicity assays as described below. In order to compare the $^{51}$Cr release and FATAL assays, all experiments were performed in parallel.

$^{15}$Cr Release Assay

A standard $^{51}$Cr release assay was performed as previously described (Ogg et al., 1998). Peptide pulsed, CMV pp65-rVV infected and control targets for use in the $^{51}$Cr release assay were labeled with 100 μCi $^{51}$Cr as sodium chromate ($Na_2^5$ $CrO_4$), (New England Nuclear, Boston, Mass.) and incubated for 1 h (37° C., 5% $CO_2$). Target cells were washed three times in R-15 medium (RPM1 1640 media supplemented with 15% heat inactivated fetal calf serum, L-glutamine, HPEPS, and penicillin-streptomycin (Biowhittaker)) and aliquoted in duplicate at 5×10$^3$ cells per well into 96-well U-bottom plates (Becton Dickinson Labware, Franklin Lakes, N.J.). To compare the relative sensitivity of the $^{51}$Cr and FATAL assays, CMV-pp65 specific CD8$^+$ T cells were incubated at various ratios with target cells. The assay was incubated at 37° C., 5% $CO_2$ for up to 5 hours. After the assay incubation period, 30 μl of the supernatant was harvested from each well into corresponding wells of a 96-well LumaPlate (Packard Instruments, Downers Grove, Ill.). The gamma irradiation from each well was assessed in a TopCount Microplate Scintillation Counter (Packard Instruments). For the $^{51}$Cr release assays, the percent specific lysis was calculated by the following equation:

Percent specific LYSIS=(test release−spontaneous release/maximum release−spontaneous release)×100.

All the assays were performed in duplicate.

Flow Cytometric Assay

Antigen labeled and control target cells for use in the FATAL assay were labeled with PKH-26 according to the manufacturer's instructions (Sigma, St. Louis, Mo.). 1×10$^6$ target cells were stained with PKH-26 (final concentration of 2.5×10$^{-6}$ M) at room temperature for 3–5 min. To stop the reaction a volume of heat inactivated fetal calf serum (FCS) equal to that of the cells and dye, was added to the cell suspension, then incubated for 1 min at room temperature before centrifugation for 5 minutes at 400× g. After a single wash with 10 ml PBS, the target cells were centrifuged for 5 minutes and the supernatant was discarded. PKH-26 labeled target cells were then labeled with 5-(and-6)-carboxyfluorescein diacetate succinimidyl ester (CFSE) (Molecular Probes, Eugene, Oreg.). CFSE was diluted to a final concentration of 2.5×10$^{-6}$ M and added to the target cells suspension immediately following the addition of the CFSE, an equal volume of FCS was added to stop the reaction and cells were centrifuged for 5 minutes at room temperature. Finally, the target cells were washed twice with PBS, resuspended in R-15 medium, and dispensed in duplicate at 5×10$^3$ cells per well into 96-well U-bottom plates (Becton Dickinson). Effector cells were added at various E:T ratios and mixed with the target cells.

The FATAL assay was incubated up to 5 hours at 37° C., 5% $CO_2$ in parallel with the $^{51}$Cr release assay. Following incubation, the total contents of the U bottom plate were transferred to a 96-well V-bottom plate (Becton Dickinson, Lincoln Park, N.J.) and centrifuged for 5 minutes at room temperature. The supernatant was discarded and the cell pellet was resuspended in 150 μl 1% paraformaldehyde and analyzed by flow cytometry within 24 hours.

Flow Cytometry

Flow cytometry was performed with a FACS Calibur (Becton Dickinson, San Jose, Calif.) equipped with an argon laser operating at 488 nm. Fluorescence was collected through a 530/25 nm filter for CFSE emission and through a 585/40 nm filter for PKH-26. The contents of each FATAL assay well (150 μl) were acquired and no gating was used for acquisition. A threshold was set on forward light scatter and side light scatter to exclude a group of very small scatter signals at the lower left corner of the plot, previously characterized as subcellular fragments (Bartkowiak et al., 1999). Data was subsequently analyzed via CellQuest software (Becton Dickinson).

Results

Labeling with PKH-26 and CFSE is Uniform and Does not Affect Cell Viability.

Figure 1C:
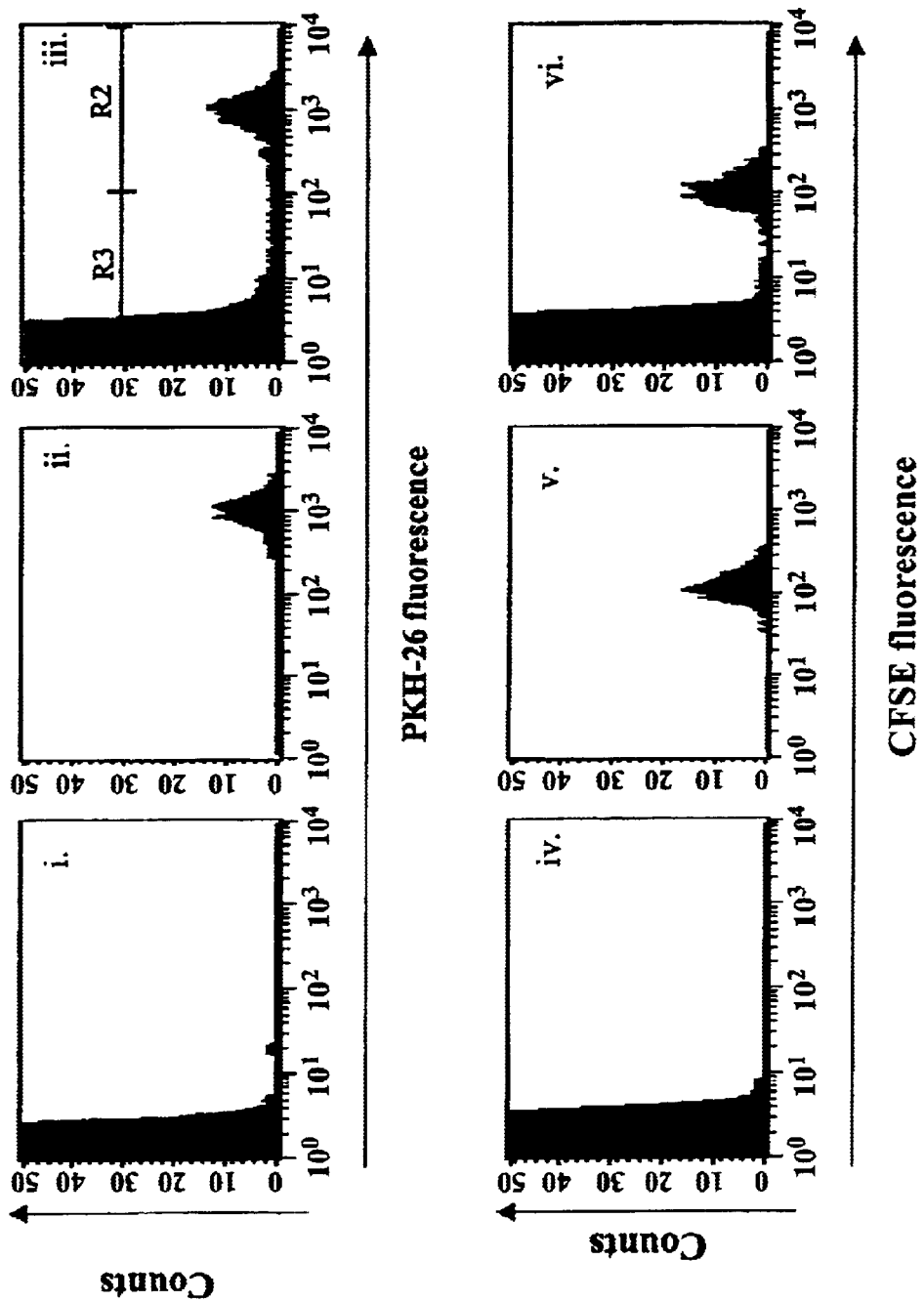
Figure 1D:
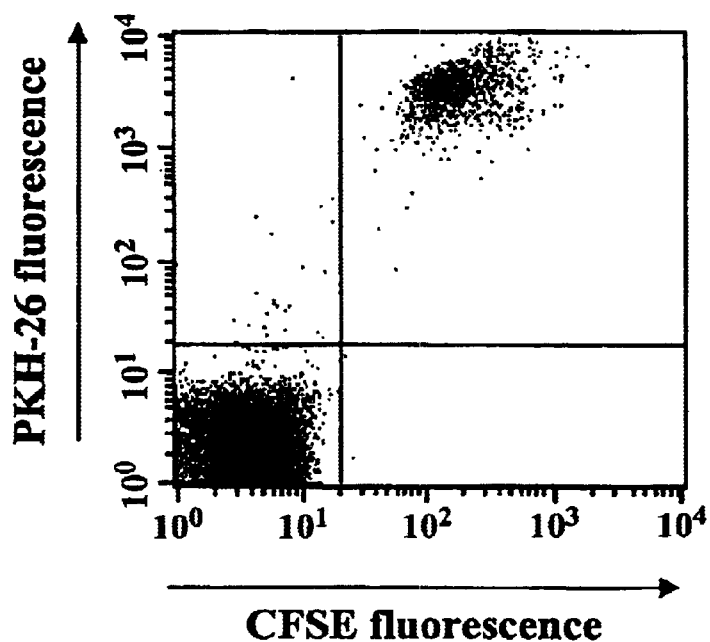

To determine the efficiency of labeling, BCL were stained with PKH-26/CFSE in combination and then analyzed by flow cytometry. The staining of BCL target cells is shown in FIG. 1, with quadrant positions and instrument settings that were defined by unstained target cells. FIG. 1a shows a forward scatter/side scatter (FSC/SSC) dot plot and an R1 gate determined by target cells incubated in media alone. BCL were stained with either PKH-26 or CFSE alone (FIG. 1b) and the resulting histogram plots are shown in FIG. 1c. Color compensations were set using standard procedures (Loken and Lanier, 1984). The analysis markers were adjusted to exclude autofluorescence found to the left of the cursors defining the target population.

Target Cell Labeling and Calculation of Specific Cell Lysis as Detected by the FATAL Assay.

PKH-26/CFSE double stained BCL target cells were co-cultured with non-stained effector cells. FIG. 1c shows histogram displays of BCL autofluorescence (FIG. 1c(i,iv)), the CFSE and PKH-26 fluorescence of control targets alone (FIG. 1c(ii,v)) and targets co-incubated with effector cells (FIG. 1c(iii,vi)). Histograms FIG. 1c(iii) and FIG. 1c(vi) show two exclusive peaks, confirming the clear identification of two separate populations. There was no change in the mean position of the two peaks in the co-cultured sample from the single stained controls indicating that there was no transfer of PKH-26 or CFSE to the effector cell population. The assessment of antigen specific cell lysis as detected by the FATAL assay was determined by the percentage of labeled target cells surviving following a 4-hour incubation with effector cells. Target cells incubated in the absence of effector cells (spontaneous release of CFSE) were used for comparative analysis. Initially, a forward scatter/side scatter (FSC/SSC) dot plot was drawn (FIG. 1a), and live gate (R1) was adjusted to include viable cells.

Figure 2:
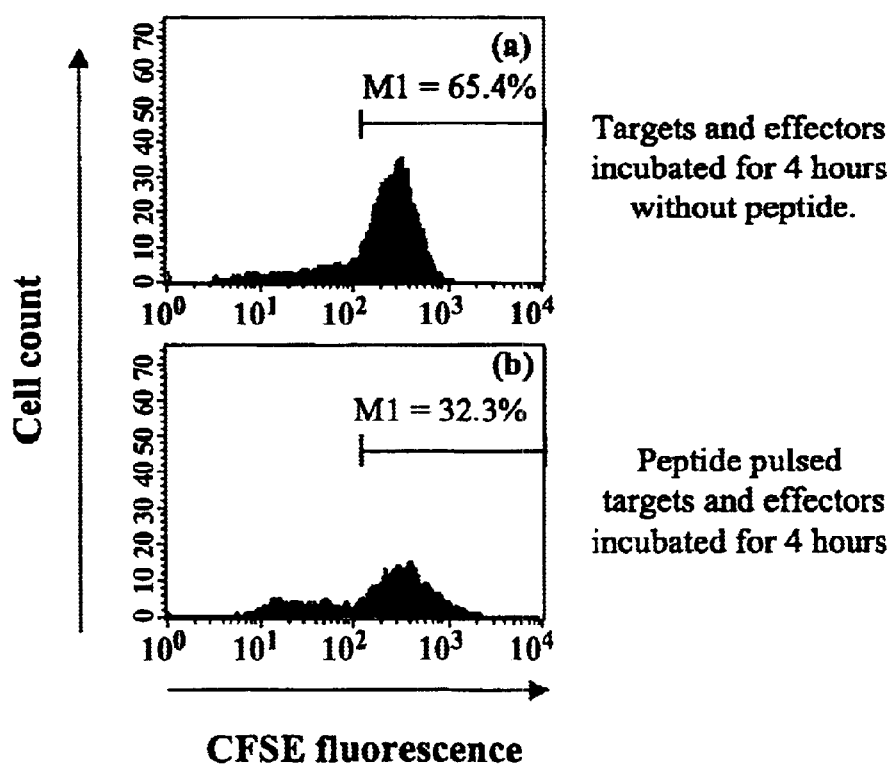
FIG. 2 depicts lysis of peptide-pulsed target cells stained with CFSE and PKH-26.

This determination is made by the analysis of target cells incubated alone with media in the assay plate. From the R1 live gate a PKH-26 histogram (FIG. 1c(iii)) is derived, which distinguishes the target (R2) and effector (R3) cell populations. The discrimination of target cells from effector cells permits the calculation of an actual E:T ratio for each condition (FIG. 1c(iii)). A second histogram displays the CFSE fluorescence (FIG. 2) of the target cells identified by the PKH-26$^{Hi}$ gate (R2). Cells contained within the PKH-26$^{Hi}$ and CFSE$^{Hi}$ double positive gate represent viable target cells. A marker (M1) was set using control conditions so that the CFSEHi viable target cell population included >98% of the target cells incubated in media alone. The percentage of specific cell lysis in the viable target cell population was determined by the disappearance of the antigen labeled targets from CFSE$^{Hi}$ population when compared to the CFSE$^{Hi}$ fluorescence of control targets. The position of the PKH-26$^{Hi}$ and CFSE$^{Hi}$ gates was maintained throughout the analysis.

Therefore, to calculate the percentage of specific lysis using the FATAL assay (FIG. 2): Percent SURVIVAL= (mean CFSE$^{Hi}$ percent of test well/mean CFSE$^{Hi}$ percent of spontaneous release)×100. Percent specific LYSIS=100-% survival.

PKH-26/CFSE Staining is Retained Significantly Longer than $^{51}$Cr Labeling.

Figure 3:
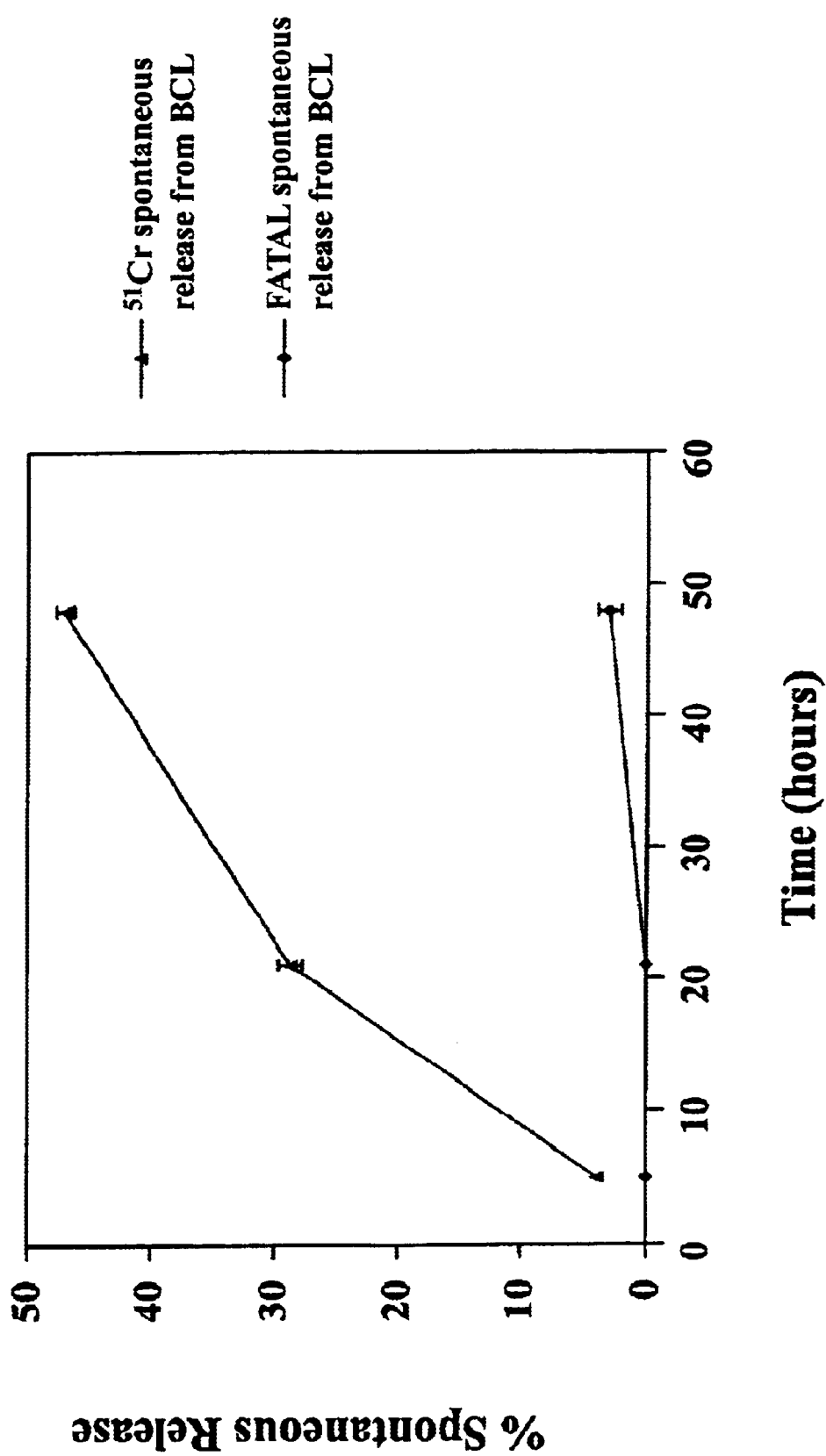
FIG. 3 is a graph depicting spontaneous release of CFSE and $^{51}$Cr from labeled cells.

To compare the leakage of $^{51}$Cr and PKH-26/CFSE, BCL were labeled and spontaneous release monitored over a 45-h period. Labeled target cells were aliquoted at 1×10$^4$ cells per well and the results are graphically represented in FIG. 3. The overall leakage of PKH-26 and CFSE from cells incubated at 37° C., 5% $CO_2$ was forty fold lower than that found for $^{51}$Cr following a 45-hour incubation. Spontaneous release of $^{51}$Cr over 30% is sufficient to invalidate an assay, limiting $^{51}$Cr release assays to less than 18 hours. Following the 45-hour incubation, the leakage of PKU-26/CFSE was less than 5%, indicating that PKH26 and CFSE are viable components of a short or long term cytolysis assay.

Figure 4:
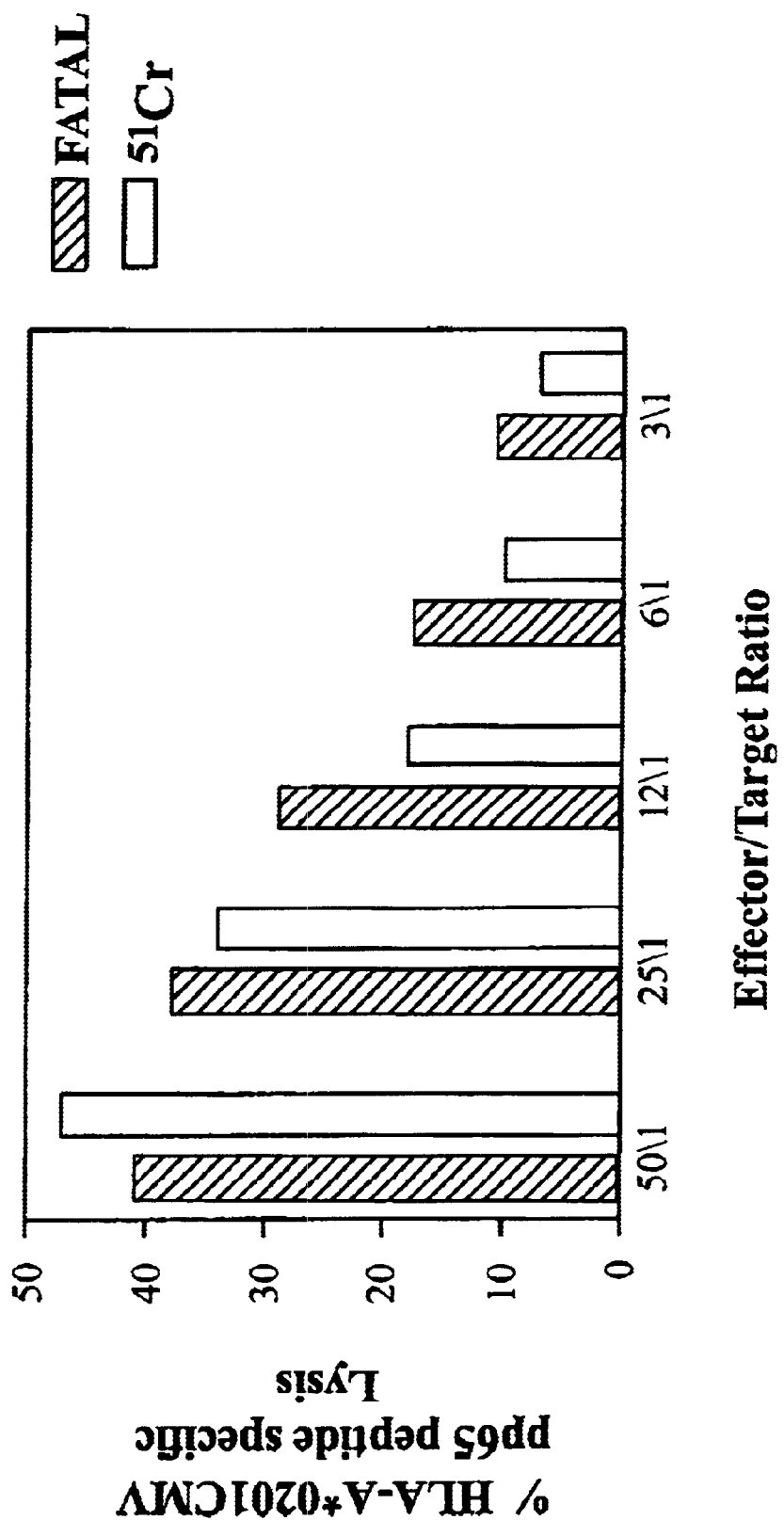
FIG. 4 is a graph depicting peptide-specific lysis of CFSE- or $^{51}$Cr-labeled target cells.
Figures 5A, 5B:
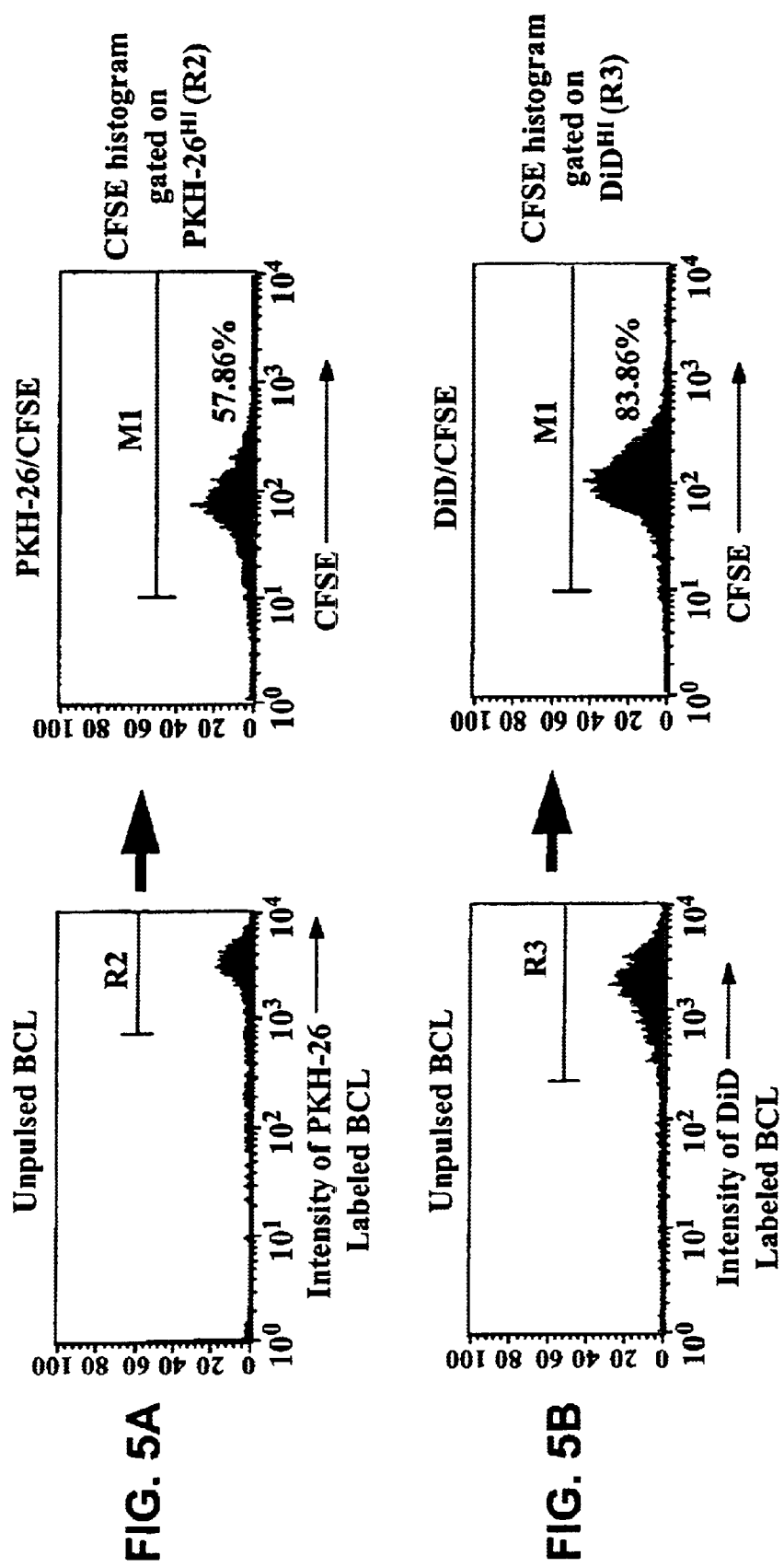
FIGS. 5A and B depict FACS plots showing staining of donor BCL with CFSE and either PKH-26 (FIG. 5A) or DiD (FIG. 5B), and analysis of each stained cell population individually.

Comparison of Specific Target Cell Lysis Between the FATAL and $^{51}$Cr Release Assays A direct comparison of cytotoxic activity measured by the FATAL and $^{51}$Cr release assays was performed concurrently using identical antigen specific effector, target cells and E:T ratios. Both the FATAL and $^{51}$Cr release assay results are displayed in FIG. 4. These data represent the mean of duplicate samples. It can be seen that at high E:T ratios the percentage of lysed target cells in the $^{51}$Cr release assay is higher than that seen using the FATAL assay. Importantly, at lower E:T ratios the FATAL assay detected a greater degree of viable target cell lysis. Regression analysis demonstrated a significant correlation between the lysis detected by the two assays (r2=0.998, P<0.0001).

Additionally, target cells were infected with rVV overnight and subsequently labeled with PKH-26/CFSE or $^{51}$Cr prior to incubation with antigen specific effector cells. Analysis of specific cell lysis detected by FATAL or $^{51}$Cr indicated that the techniques were comparable.

Example 2

Antigen-Specific Lysis of Dual Target Cells Labeled with PKH-26 or DiD and CFSE.

This example describes an assay termed "Dual Target assay".

Materials and Methods

Generation of Effector Cells

To evaluate antigen specific CD8$^+$ T-cell effector activity, Influenza matrix protein-specific CTLs were used as effector cells and B-lymphoblastoid cell lines (BCL) as target cells. Several influenza HLA A*0201 peptide (GILGFVFTL SEQ ID NO:3) specific semi-clones from an HLA-A*0201, donor were generated as previously described (Wills et al. (1996) J. Virol. 70:7569–7579).

Preparation of Target Cell Populations

The dual target assay was performed using the same autologous immortalized BCL from an HLA-A*0201 individual. The BCL were incubated with 10 μg/ml of the HLA-A*0201 restricted influenza HLA A*0201 peptide (GILGFVFTL SEQ ID NO:3) peptide for 1 hour at 37° C. in 5% $CO_2$ prior to use in the assays. In addition, target BCL were incubated without peptide as background inter- and intra-assay controls. All target cells were washed once in PBS, centrifuged for 5 minutes at 400 g, the supernatant was discarded and cells were resuspended prior to use. (Biowhittaker, Walkersville, Md.). The cell number and viability were assessed by trypan blue exclusion (Biowhittaker). The antigen labeled target and control cells were subsequently used in the Dual Target Assay as described below.

Flow Cytometric Assay

Peptide labeled and control target cells for use in the FATAL assay were labeled with PKH-26 or DiD (1,1'-dioctadecyl-3,3,3',3'-tetramethylindodicarbocyanine perchlorate) according to the manufacturer's instructions (Sigma, St. Louis, Mo. and Molecular Probes, Eugene, Oreg. respectively). 1×10$^6$ target cells were stained with PKH-26 (final concentration of 2.5×10$^{-6}$ M) at room temperature for 3–5 minutes. To stop the reaction, a volume of heat-inactivated fetal calf serum (FCS) equal to that of the cells and dye was added to the cell suspension, then incubated for 1 minute at room temperature before centrifugation for 5 minutes at 400× g. After a single wash with 10 ml PBS, the target cells were centrifuged for 5 minutes and the supernatant was discarded. 1×10$^6$ target cells were stained with DiD (final concentration of 1×10$^{-6}$ M) at room temperature for 5–10 min. To stop the reaction, a volume of heat-inactivated fetal calf serum (FCS) equal to that of the cells and dye was added to the cell suspension, then incubated for 1 minute at room temperature before centrifugation for 5 minutes at 400× g. After a single wash with 10 ml PBS, the target cells were centrifuged for 5 minutes and the supernatant was discarded.

DiD or PKH-26 labeled target cells were then labeled with 5-(and-6)-carboxyfluorescein diacetate succinimidyl ester (CFSE) (Molecular Probes, Eugene, Oreg.). CFSE was diluted to a final concentration of $2.5 \times 10^{-6}$ M and added to the target cells suspension. Immediately following the addition of the CFSE, an equal volume of FCS was added to stop the reaction and cells were centrifuged for 5 minutes at room temperature. Finally, the target cells were washed twice with PBS, resuspended in R-15 medium, and dispensed in duplicate at $5 \times 10^3$ cells per well into 96-well U-bottom plates (Becton Dickinson). Effector cells were added at various E:T ratios and mixed with the target cells.

The Dual target assay was incubated up to 5 hours at 37° C., 5% $CO_2$. Following incubation, the total contents of the U bottom plate were transferred to a 96-well V-bottom plate (Becton Dickinson, Lincoln Park, N.J.) and centrifuged for 5 minutes at room temperature. The supernatant was discarded and the cell pellet was resuspended in 100 μl 1% paraformaldehyde and analyzed by flow cytometry within 24 hours.

Flow Cytometry

Flow cytometry was performed with a FACS Calibur (Becton Dickinson, San Jose, Calif.) equipped with an argon laser operating at 488 nm. Fluorescence was collected through a 530/25 nm filter for CFSE emission, through a 585/40 nm filter for PKH-26 and a 661/16 filter for DiD. The contents of each Dual Target Assay well (100 μl) were acquired and no gating was used for acquisition. A threshold was set on forward light scatter and side light scatter to exclude a group of very small scatter signals at the lower left corner of the plot, previously characterized as subcellular fragments (Bartkowiak et al., 1999). Data were subsequently analyzed via CellQuest software (Becton Dickinson).

Results

The results are shown in FIGS. 5–8. FIGS. 5A and 5B depict FACS plots showing staining of donor BCL with CFSE and either PKH-26 (FIG. 5A) or DiD (FIG. 5B), and analysis of each stained cell population individually. Donor BCL were stained with CFSE and either PKH-26 (A) or DiD (B) and incubated for 4 hours at 37 C independently. Regions R1 and R2 are gated on PKH-26 and DiD respectively. The percentage of CFSE present in the double stained populations was obtained by drawing a marker region (M1) on the CFSEHi population.

Figure 6:
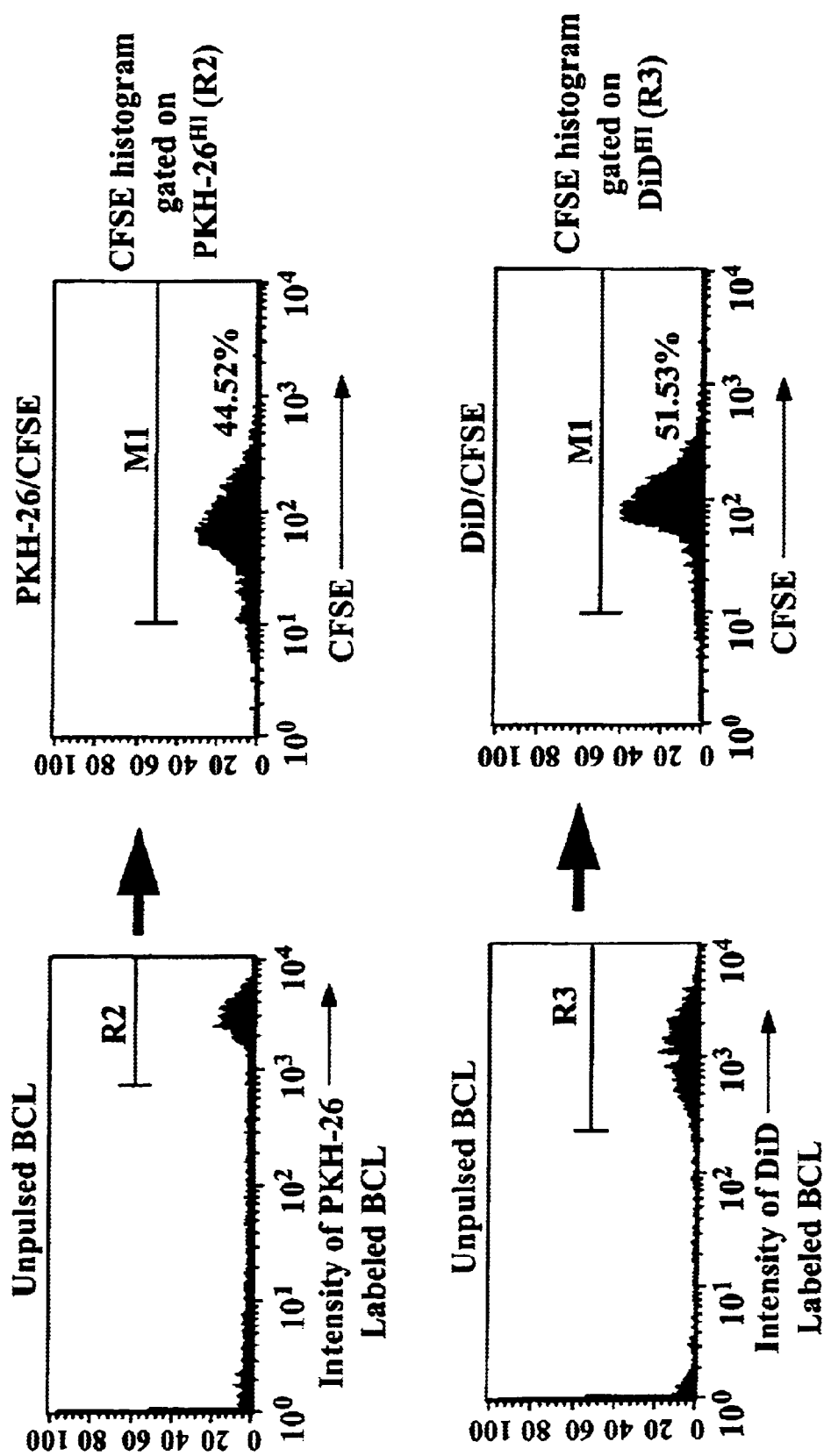
FIG. 6 depicts results showing that dual-labeled target cells are readily distinguishable in mixed populations using flow cytometry.

FIG. 6 presents results showing that dual-labeled target cells are readily distinguishable in mixed populations using flow cytometry. Donor BCL were stained with CFSE and either PKH-26 or DiD. The two sets of targets were then co-incubated for 4 hours at 37 C. The percentage of CFSE present in the double stained populations was obtained by drawing a marker region (M1) on the $CFSE^{Hi}$ population. FIG. 6 depicts the CFSE histogram gated on PKH-26$^{Hi}$ (upper right panel) or gated on DiD$^{Hi}$ (lower right panel). Here we demonstrate that the signal of both dyes in the same culture can be distinguished by the appearance in FL-2 and FL-4 for PKH-26 and DiD, respectively.

Figure 7:
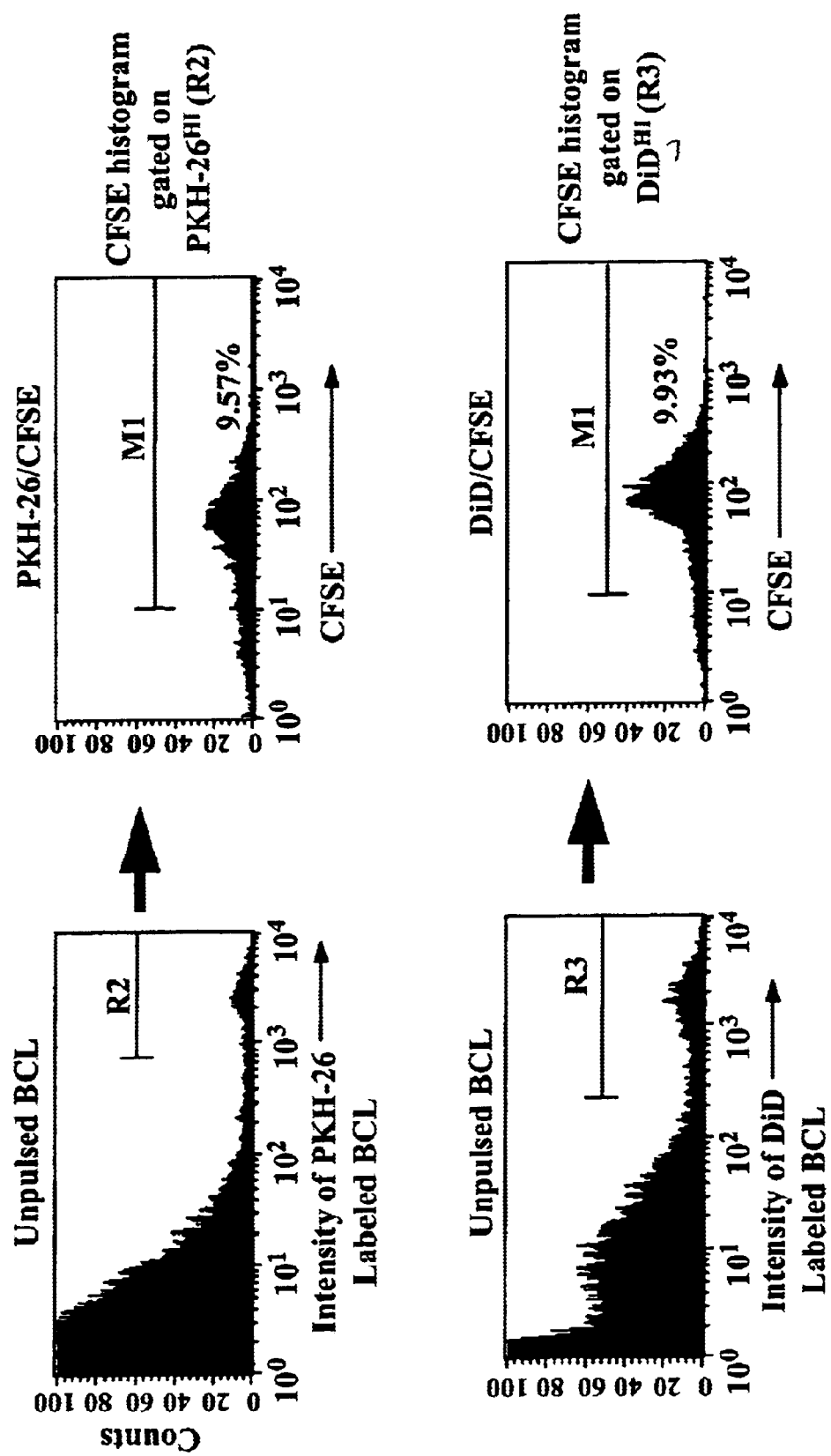
FIG. 7 depicts the results of contacting unpulsed labeled target cells with a lytic agent.

FIG. 7 shows the results of contacting unpulsed labeled target cells with a lytic agent. Donor BCL were stained with CFSE and either PKH-26 or DiD. The two sets of targets were then co-incubated for 4 hours at 37 C in the presence of autologous influenza matrix HLA-A*0201 peptide specific T-cells. Regions R1 and R2 are gated on PKH-26 and DiD, respectively. The percentage of CFSE present in the double stained populations was obtained by drawing a marker region (M1) on the $CFSE^{Hi}$ population. This "unpulsed" coculture represents the background lysis of targets in the absence of specific Influenza matrix HLA-A*0201 peptide lysis.

Figure 8:
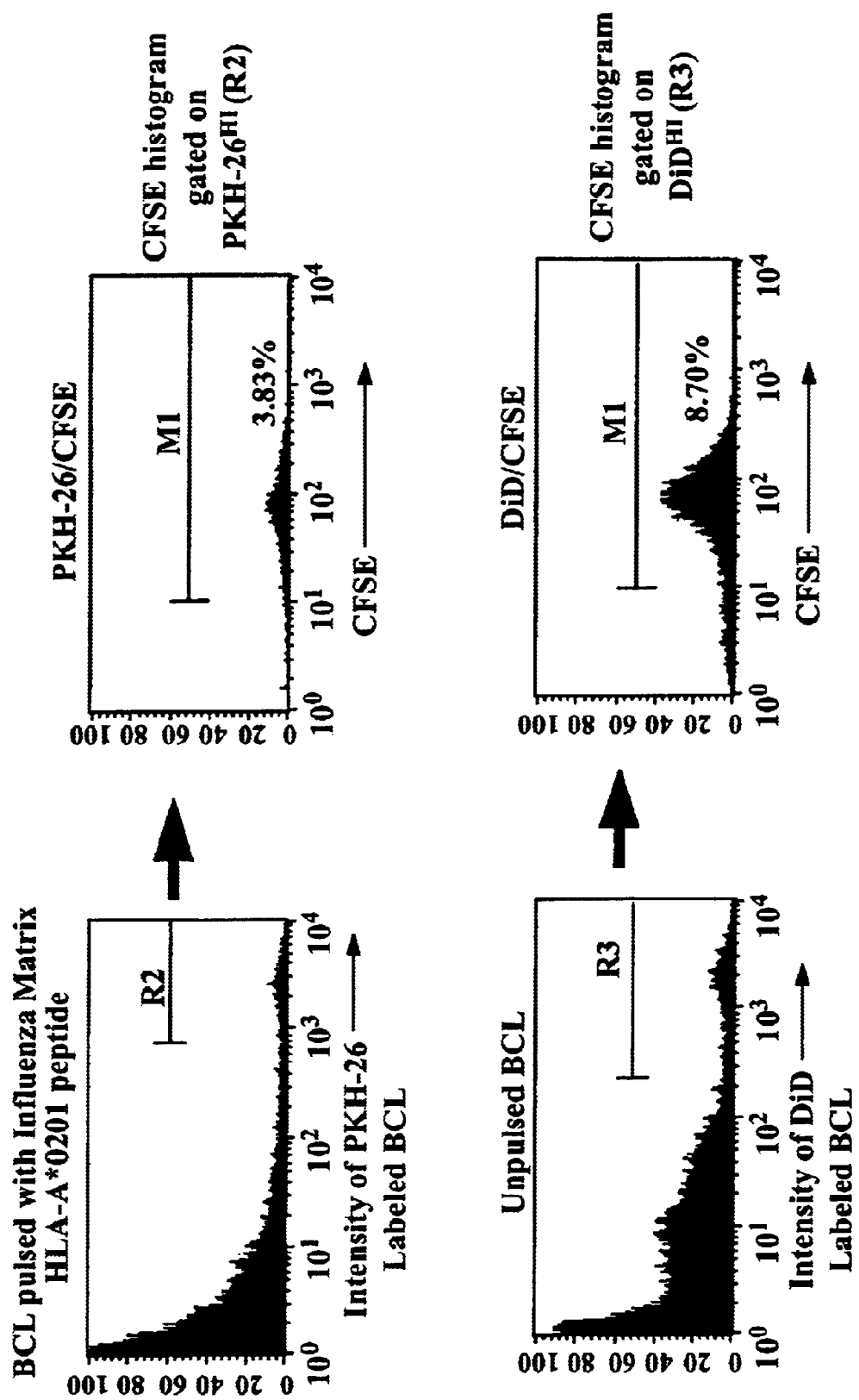
FIG. 8 depicts the results of contacting peptide-pulsed labeled target cells with a lytic agent.

FIG. 8 shows the results of contacting peptide-pulsed labeled target cells with a lytic agent. Two populations of donor BCL were incubated with or influenza matrix HLA-A*0201 peptide for 1 hour (pulsed). The peptide pulsed BCL were stained with CFSE and PKH-26, whereas the unpulsed BCL were stained with CFSE and DiD. The two sets of targets were then co-incubated (E) for 4 hours at 37 C in the presence of autologous influenza matrix HLA-A*0201 peptide specific T-cells. Following the incubation period, the percentage of labeled BCL was calculated for each stained population by comparison with unpulsed BCL incubated with effector T-cells (D). The percentage survival for each of the targets in the dual target assay was calculated using the equation: (% of $CFSE^{Hi}$ (M1) of the PKH-26 or DiD costained populations (E)/% of $CFSE^{Hi}$ (M1) of the PKH-26 or DiD costained populations (D))×100. The percentage lysis is obtained by subtracting the percentage survival from 100. The example given here cocultures D and E is: (3.83/9.57)×100=40% survival. Therefore 60% of the target cells labeled with PKH-26/CFSE were lysed.

The above demonstrate that the invention provide methods for detecting specific cell lysis. These methods involve the labeling methods that eliminate the use of radioactivity, as required in previous $^{51}Cr$ release assays, and provide the advantages of uniform labeling of virtually all cell types to produce a bright and distinct labeled target cell population which is easily identified by flow cytometry. Lysis of the labeled target population using the methods of the present invention is readily detected, as the cytosolic label has a very low rate of spontaneous leakage, and, when membrane damage occurs, the dye is almost instantaneously lost and the cells are no longer able to take up or retain the dye. These assay methods provide detailed information about both target and effector cells at a single cell level, and are more sensitive that $^{51}Cr$ release assays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting specific lysis of a target cell, comprising:
   a) contacting a labeled viable target cell with a lytic agent, wherein the target cell is labeled with a first plasma membrane-labeling fluorescent dye that labels the plasma membrane of the target cell and a first cytosol-labeling fluorescent dye that labels the cytosol of the target cell; and
   b) determining the amount of the cytosol-labeling fluorescent dye remaining in the target cell, wherein a reduction in the amount of the cytosol-labeling fluorescent dye in the target cell when the target cell is contacted with the lytic agent, compared to the amount of cytosol-labeling fluorescent dye in a control target cell not contacted with the lytic agent, indicates that the target cell is lysed by the lytic agent, and wherein said first plasma membrane-labeling fluorescent dye has detectably different spectral properties from the first cytosol-labeling fluorescent dye such that the first plasma membrane-labeling fluorescent dye is distinguishable from the first cytosol-labeling fluorescent dye.

2. The method of claim 1, wherein said first plasma membrane-labeling fluorescent dye is a lipid-associated fluorescent dye, and wherein said first cytosol-labeling fluorescent dye is a fluorescent dye that labels proteins in the cytosol.

3. The method of claim 1, wherein the lytic agent is a cell having lytic activity toward the target cell.

4. The method of claim 3, wherein the cell having lytic activity toward the target cell is an antigen-specific CD8$^+$ T lymphocyte, and the target cell displays the antigen in an MHC Class I molecule on its cell surface.

5. The method of claim 1, wherein the lytic agent is an antibody specific for a cell surface marker on the target cell.

6. The method of claim 1, wherein the lytic agent comprises an antibody specific for a cell surface marker on the target cell, and a lytic cell having an Fc receptor, wherein the lytic cell is selected from the group consisting of a neutrophil, an eosinophil, a macrophage, a monocyte, and a natural killer cell.

7. The method of claim 1, wherein the emission of the frst plasma membrane-labeling fluorescent dye differs from the emission of the first cytosol-labeling fluorescent dye by at least about 10 nm.

8. The method of claim 2, wherein the lipid-associated fluorescent dye is selected from PKH-26, PKH-67, and a long chain dialkylcarbocyanine.

9. The method of claim 2, wherein the protein-labeling cytosol dye is selected from 5-(-6)-carboxyfluorescein, 5-(-6)(((4-chloromethyl)benzoyl)amino) tetramethylrhodamine), 7-amino-4-chloromethylcoumarin, and a SNARF® fluorescent dye.

10. The method of claim 1, wherein the amount of cytosol-labeling fluorescent dye in the target cell is determined using flow cytometry.

* * * * *